United States Patent
Avraham et al.

(10) Patent No.: US 12,373,283 B2
(45) Date of Patent: Jul. 29, 2025

(54) ERROR CORRECTION SYSTEMS AND METHODS FOR DNA STORAGE

(71) Applicant: Western Digital Technologies, Inc., San Jose, CA (US)

(72) Inventors: David Avraham, Even Yehuda (IL); Ran Zamir, Ramat Gan (IL); Alexander Bazarsky, Holon (IL)

(73) Assignee: Western Digital Technologies, Inc., San Jose, CA (US)

( * ) Notice: Subject to any disclaimer, the term of this patent is extended or adjusted under 35 U.S.C. 154(b) by 0 days.

(21) Appl. No.: 18/356,104

(22) Filed: Jul. 20, 2023

(65) Prior Publication Data

US 2024/0193037 A1    Jun. 13, 2024

Related U.S. Application Data

(60) Provisional application No. 63/430,996, filed on Dec. 7, 2022.

(51) Int. Cl.
| | |
|---|---|
| *G06F 11/00* | (2006.01) |
| *G06F 11/10* | (2006.01) |
| *G16B 30/00* | (2019.01) |
| *G16B 50/30* | (2019.01) |

(52) U.S. Cl.
CPC .......... *G06F 11/1004* (2013.01); *G16B 30/00* (2019.02); *G16B 50/30* (2019.02)

(58) Field of Classification Search
CPC .................................................. G06F 11/1004
See application file for complete search history.

(56) References Cited

U.S. PATENT DOCUMENTS

| | | | | |
|---|---|---|---|---|
| 9,158,621 | B2 * | 10/2015 | Sharon | G11C 29/52 |
| 10,002,042 | B2 * | 6/2018 | Alrod | G06F 3/0688 |
| 10,020,826 | B2 | 7/2018 | Gladwin et al. | |
| 10,103,748 | B2 * | 10/2018 | Hsu | H03M 13/00 |
| 10,419,024 | B2 * | 9/2019 | Xiong | H04L 1/0057 |

(Continued)

OTHER PUBLICATIONS

Press WH, Hawkins JA, Jones SK Jr, Schaub JM, Finkelstein IJ., "Hedges error-correcting code for DNA storage corrects indels and allows sequence constraints." Proc Natl Acad Sci U S A., Aug. 4, 2020;117(31):18489-18496. doi: 10.1073/pnas.2004821117.

*Primary Examiner* — Esaw T Abraham
(74) *Attorney, Agent, or Firm* — DENTONS Durham Jones Pinegar

(57) ABSTRACT

A DNA-based storage system includes an error correction system operable to: (a) identify a DNA codeword from a DNA sequencing operation; (b) calculate an initial syndrome weight; (c) determine that the initial syndrome weight is greater than a predetermined threshold; (d) perform an alignment alteration in the information segment by: (i) selecting a skew point within the information segment; (ii) performing an indel operation on the information segment at the skew point; (iii) calculating a modified syndrome weight; (iv) comparing the initial syndrome weight with the modified syndrome weight; and (v) incorporating the indel operation into the information segment when the comparing indicates an improvement in the modified syndrome weight; (e) decode the modified codeword; and (f) transmit the contents of the output file to a computing device, the output file representing user data stored within the DNA molecule.

20 Claims, 9 Drawing Sheets

(56) References Cited

U.S. PATENT DOCUMENTS

| | | | |
|---|---|---|---|
| 10,725,860 B2 | 7/2020 | Avraham et al. | |
| 10,902,939 B2 * | 1/2021 | Merriman | G16B 50/40 |
| 10,963,469 B2 | 3/2021 | Taig et al. | |
| 11,100,404 B2 | 8/2021 | Merriman et al. | |
| 11,449,236 B2 | 9/2022 | Avraham et al. | |
| 11,515,897 B2 * | 11/2022 | Cho | G06F 3/0679 |
| 2007/0042372 A1 * | 2/2007 | Arita | B82Y 10/00 |
| | | | 435/6.12 |
| 2018/0013445 A1 * | 1/2018 | Hsiao | H03M 13/451 |
| 2020/0321079 A1 | 10/2020 | Huang et al. | |
| 2022/0042070 A1 | 2/2022 | Eppler et al. | |
| 2022/0166446 A1 * | 5/2022 | Yekhanin | H03M 7/6041 |
| 2022/0237470 A1 | 7/2022 | Vishwakarma et al. | |

* cited by examiner

ERROR CORRECTION SYSTEMS AND METHODS FOR DNA STORAGE

CROSS-REFERENCE TO RELATED APPLICATIONS

The present application claims priority to U.S. Provisional Application 63/430,996 entitled "ERROR CORRECTION SYSTEMS AND METHODS FOR DNA STORAGE", filed Dec. 7, 2022, the entire disclosure of which is hereby incorporated by reference in its entirety.

BACKGROUND

DNA-based storage systems are emerging as a promising storage technology. DNA is a long molecule made up of four nucleotide bases—adenine (A), cytosine (C), thymine (T) and guanine (G). For storage purposes, base units (ACTG) of synthesized DNA can be used to encode information—similar to how a string of ones and zeros represent data in traditional electronic storage systems. The encoded information may then be stored, subsequently accessed and decoded.

For example, DNA-based storage systems typically store DNA data using three main processes—synthesis (or writing) in which the base units of synthesized DNA are joined together to produce a desired DNA string; storage, in which the DNA string is stored in a DNA-based storage medium; and sequencing (or reading), in which the DNA string is translated to binary/digital data.

While DNA-based storage systems are more dense than traditional electronic data storage systems, DNA-based storage systems are more prone to errors. For example, during synthesis, storage and/or sequencing, various symbols in the DNA string may be inserted or deleted (errors known as an "indels," for "insertions" or "deletions"). In other examples, during synthesis, storage and/or sequencing, one symbol (or multiple symbols) in the DNA string may be substituted for another symbol (errors known as "substitutions").

One challenge with "indel" type errors are that any insertion or deletion can shift the data enough to generate high bit error rates, where an alignment shift of the bit stream just one to the left or one to the right can cause the data to be unrecognizable over the original data. Accordingly, what is needed is a DNA storage system that can detect and resolve such errors.

SUMMARY

The present application describes a DNA-based storage system that includes an error correction system operable to identify a DNA codeword from an output string produced from a DNA sequencing operation on a DNA molecule. In an example, the DNA codeword includes at least an information segment and an associated error correction segment. The error correction system calculates an initial syndrome weight for the information segment based on error correction data included in the error correction segment. The error correction system may also determine whether the initial syndrome weight is greater than a predetermined threshold. Based on determining the initial syndrome weight is greater than the predetermined threshold, the error correction system performs an alignment alteration in the information segment by selecting a skew point within the information segment and performing an indel operation on the information segment at the skew point, thereby generating a modified information segment. The error correction system also calculates a modified syndrome weight of the modified information segment based on the error correction data, compares the initial syndrome weight with the modified syndrome weight and incorporates the indel operation into the information segment when the comparing indicates an improvement in the modified syndrome weight. As a result, a modified codeword is generated. The error correction system may also decode the modified codeword to generate at least a portion of an output file. In an example, the portion of the output file includes data decoded from the modified information segment. The error correction system may also transmit contents of the output file to a computing device. In an example, the output file represents user data stored within the DNA molecule.

The present application also describes a method for performing error correction on a DNA codeword generated through sequencing a DNA molecule. In an example, the method includes identifying a DNA codeword from an output string produced from a DNA sequencing operation on a DNA molecule. In an example, the DNA codeword includes at least an information segment and an associated error correction segment. The method also includes calculating an initial syndrome weight for the information segment based on error correction data included in the error correction segment and determining whether the initial syndrome weight is greater than a predetermined threshold. Based on determining the initial syndrome weight is greater than the predetermined threshold, an alignment alteration is performed in the information segment by selecting a skew point within the information segment and performing an indel operation on the information segment at the skew point. As a result, a modified information segment is generated. The method also includes calculating a modified syndrome weight of the modified information segment based on the error correction data, comparing the initial syndrome weight with the modified syndrome weight and incorporating the indel operation into the information segment when the comparing indicates an improvement in the modified syndrome weight. As such, a modified codeword is generated.

The present application further describes a control system for a DNA-based storage system. In an example, the control system includes means for identifying a DNA codeword from an output string produced from a DNA sequencing operation on a DNA molecule. In an example, the DNA codeword includes at least an information segment and an associated error correction segment. The control system also includes means for calculating an initial syndrome weight for the information segment based on error correction data included in the error correction segment. The control system may also include means for determining that the initial syndrome weight is greater than a predetermined threshold. The control system also includes means for performing an alignment alteration in the information segment in response to the determination that the initial syndrome weight is greater than the predetermined threshold.

This summary is provided to introduce a selection of concepts in a simplified form that are further described below in the Detailed Description. This summary is not intended to identify key features or essential features of the claimed subject matter, nor is it intended to be used to limit the scope of the claimed subject matter.

BRIEF DESCRIPTION OF THE DRAWINGS

Non-limiting and non-exhaustive examples are described with reference to the following Figures.

DETAILED DESCRIPTION

Figure 1:
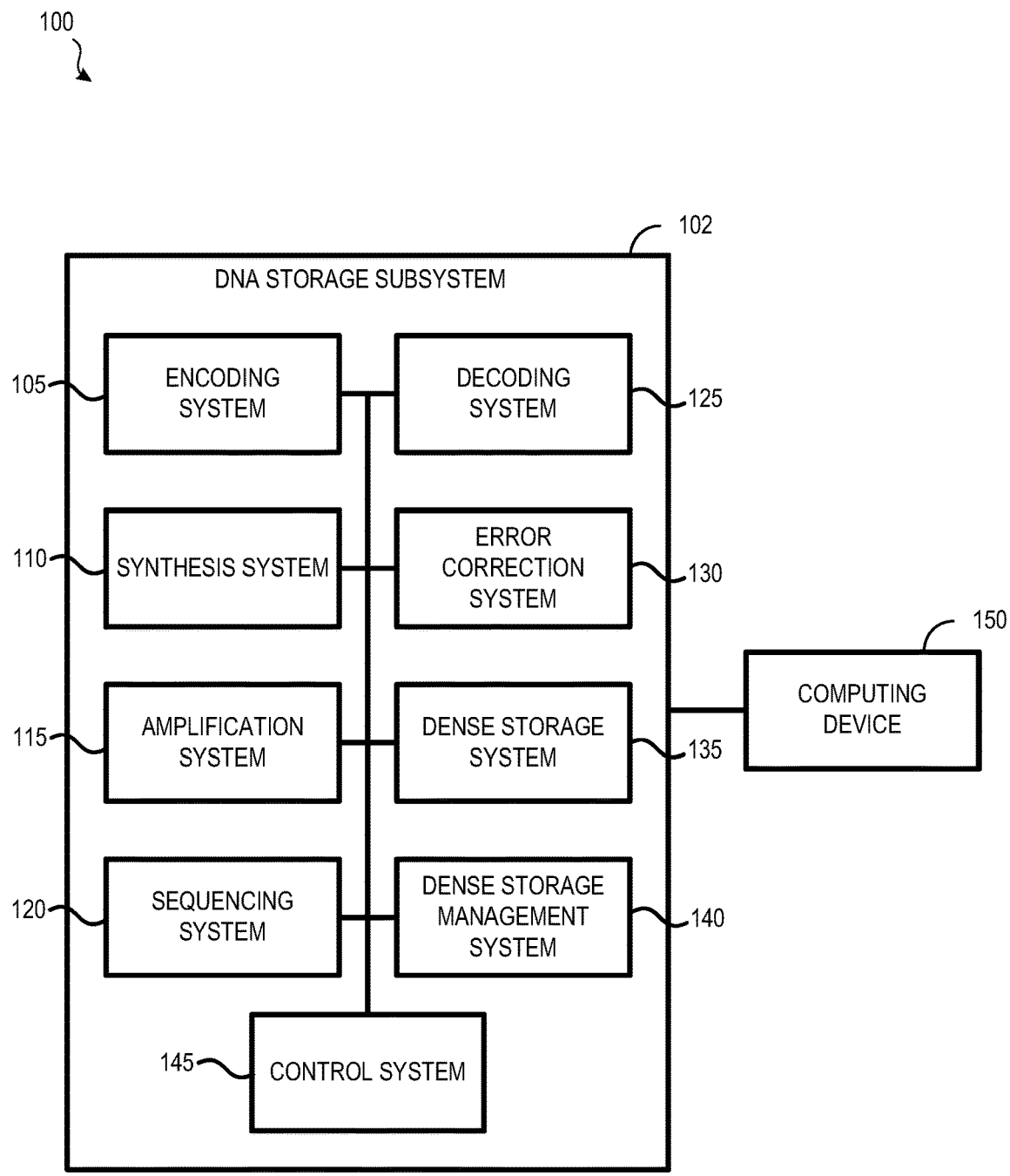
FIG. 1 illustrates a data storage system according to an example.

In the following detailed description, references are made to the accompanying drawings that form a part hereof, and in which are shown by way of illustrations specific embodiments or examples. These aspects may be combined, other aspects may be utilized, and structural changes may be made without departing from the present disclosure. Examples may be practiced as methods, systems or devices. Accordingly, examples may take the form of a hardware implementation, an entirely software implementation, or an implementation combining software and hardware aspects. The following detailed description is therefore not to be taken in a limiting sense, and the scope of the present disclosure is defined by the appended claims and their equivalents.

In a DNA storage channel, several different types of errors can occur during the synthesis and sequencing process. One example error type is a substitution error. In a substitution error, a base that was intended to be one particular DNA nucleotide (e.g., an 'A', 'T', 'G', or 'C') is swapped for one of the other nucleotides. Since most DNA encodings use these nucleotides to represent different binary values (e.g., 'A'=00, 'T'=01, 'G'=10, 'C'=11), a substitution of one nucleotide for another, if left uncorrected, may cause some of the data to be incorrectly recreated during the decoding process. However, such substitution errors are generally limited in scope to just the few bits that the erroneous base represents. Further, at least some such substitution errors can be addressed and corrected with some known error correction protocols.

In contrast, indel type errors ("inserts" and "deletes") can cause more significant issues in the DNA storage channel More specifically, insert and delete errors each involve either adding a base to, or deleting a base from, the DNA sequence. Such indel errors induce a shift in the alignment of the remaining bases. For example, a single insert error can not only introduce two additional bits into the data stream, but because the DNA sequence is an ordered structure of encoded data, this alignment shift of just one base or two bits shifts all of the other bits to the back by two places. Such misaligned data can cause the decoding operation to generate garbled data that may be useless to the end user.

In order to address such problems, the present application describes a DNA-based storage system and associated techniques for remediating indel errors after sequencing. More specifically, the DNA-based storage system inspects the initial DNA sequencing output for potential indel errors and may perform certain corrective actions to remediate those errors. In some examples, the DNA-based storage system provides an error correction system that is configured to analyze codewords of the raw sequencing output (e.g., segmented portions of the raw output, each of which contains error correction data that may be used to identify data integrity issues within the codeword). The error correction system may generate a syndrome weight for an initial codeword, where the syndrome weight provides an indication of how many error correction equations are not currently satisfied by the codeword. Further, due to the corrupting nature of indel errors, when even just one indel error occurs in a given codeword, the syndrome weight can quickly rise. If this initial syndrome weight is above a particular threshold, it may mean the one or more indel type errors are present and, as such, the error correction system performs an alignment correction process in an attempt to remediate one or more of the indel errors.

During this remediation, the error correction system searches for a skew point within the codeword, where the skew point represents the point at which the indel error has occurred. Since indel errors at a given point cause an alignment shift in the remaining bases of the codeword, this typically causes numerous bit mismatches after that skew point, thus spiking the syndrome weight. As such, the error correction system selects a potential skew point, inserts an indel error at that skew point, and then computes a new syndrome weight on the modified codeword. If the syndrome weight improves, then that is an indication that the chosen skew point and operation are likely to remediate an error that had occurred at that location. As such, the error correction system may systematically and exhaustively try each potential skew point and indel error type, retaining each corrective operation and reducing the resultant syndrome weight until the indel errors have been detected and remediated.

In some examples, the error correction system may also perform content-aware corrective actions. For example, some DNA encoding systems may use data encoding schemes that shape the resulting DNA data in certain ways, and the error correction system may use this knowledge to identify areas of potential errors. For example, if an encoding scheme is used that avoids repeating adjacent bases (e.g., "AA", "GG", or such), then the occurrence of such repeating bases indicates some type of error at or near the position of those bases. In another example, the error correction system may utilize probabilistic data about sequences that may appear within the DNA sequences. For example, the error correction system may search for patterns that have been known, historically, to be indicators of errors. When such an error pattern is detected as occurring within a codeword, the error correction system may then perform an analysis around that location of the codeword, searching for and correcting any indel errors located there.

Accordingly, the present application includes many technical benefits in the area of DNA storage and retrieval, including at least improving error detection and remediation during decoding, allowing for denser storage as fewer copies of a given DNA sequence may be needed to completely recreate the underlying data, and faster decoding as only those few copies may be sequenced and decoded.

These various benefits and examples will be described in greater detail below with reference to FIG. 1-FIG. 10.

FIG. 1 illustrates a data storage system 100 according to an example. The data storage system 100 may be used to store data that is "more dense" when compared to data that is stored in a traditional electronic storage medium such as, for example, hard disks, optical disks, flash memory, and the like. For example, the data storage system 100 may be used to store synthetic DNA-based data.

DNA includes four naturally occurring nucleotide bases: adenine (A), cytosine (C), thymine (T) and guanine (G). In order to store data in synthetic DNA, received data is encoded to the various nucleotide bases. For example, data received as ones and zeros is encoded or otherwise mapped to various sequences of the synthetic DNA nucleotide bases. Once encoded, the data may be synthesized (e.g., written) and stored (e.g., in a dense storage system). To retrieve the stored data, the synthetic DNA molecules are sequenced (e.g., read) and subsequently decoded. As part of the decoding process, the synthetic DNA nucleotide bases are remapped to the original ones and zeros. Each of these processes will be discussed in greater detail below. Effectively, the binary system of 0's and 1's (e.g., two states of a binary "base-2" numeral system, represented in one conventional binary bit) are represented in a quaternary system of A's, C's, T's, and G's (e.g., four states of a quaternary "base-4" numeral system, represented by a single nucleotide of DNA) when the source binary (e.g., base-2) data is encoded in the quaternary (e.g., base-4) system of nucleotides.

Although synthetic DNA-based data and associated DNA-based storage systems are specifically mentioned, the systems and methods described herein may be applicable to traditional electronic storage mediums/systems and/or traditional digital/binary data.

In an example, the data storage system 100 includes an encoding system 105. The encoding system 105 receives digital/binary information and/or data (e.g., binary ones and zeros, or "base-2") from a computing device (e.g., computing device 150) or from another source. This data may be referred to herein as "input data," "source data," or "original data." Such input is initially stored and represented in conventional base-2 binary (e.g., when not embodied in DNA). When the input data is received, the encoding system 105 converts or maps the ones and zeros of the original data into various DNA sequences using the synthetic DNA nucleotide bases A. C. T. and G. For example, the DNA nucleotide base "A" may be assigned a value 00, the DNA nucleotide base "C" may be assigned a value 01 (base-2), the DNA nucleotide base "T" may be assigned a value 10 and the DNA nucleotide base "G" may be assigned a value 11. These binary-to-quaternary mappings, and their complements, are used in the examples provided herein, but it should be understood that any similar mapping may be used.

In one example, the encoding system 105 performs a "direct encoding" process when preparing input data for memorialization in DNA. Direct encoding includes the binary-to-quaternary mappings to translate or convert each pair of bits into a single nucleotide. For example, input data of 010010110100 may be directly encoded as a DNA sequence or DNA string of CATGCA. This data, when embodied in DNA form, may be referred to herein as "DNA data." Such direct encoding of data yields one nucleotide of DNA data for every two bits of input data. Other more complex encoding processes are described herein.

The data storage system 100 may also include a synthesis system 110. In an example, the synthesis system 110 writes or otherwise manufactures DNA strands based on the data provided by the encoding system 105. For example, using a series of chemical steps or processes, the synthesis system 110 creates and assembles the various DNA bases (e.g., the ACTG bases) are assembled to mirror the base-4 representation determined from the encoding process. Although chemical steps or processes are mentioned, the synthesis system 110 may use other synthesis techniques, and the synthesis system 110 includes both hardware components configured to create such DNA strings as well as software and/or electronic components for controlling those hardware components.

Continuing with the example above, during synthesis, since the digital data of 010010110100 is represented as CATGCA, the synthesis system 110 would first generate and/or identify a "C" base. An "A" base would then be generated and/or identified and be attached to the "C" base. A "T" base would then be generated and/or identified and be attached to the "CA" combination that was previously generated. This process repeats until the entire DNA string (e.g., CATGCA) is created. The terms "created", "generated", or "synthesized", and their variants, may be used interchangeably herein when referring to the making of an real-world synthetic string of DNA. Further, the terms "DNA string" and "DNA sequence" may also be used interchangeably to refer to the synthetic DNA molecule created during the processes described herein, or to a mathematical representation of that DNA string, depending on context.

When the synthesis process is complete, the DNA sequence is stored in a physical storage medium such as, for example, a dense storage system 135 (e.g., one or more synthetic DNA molecules). The dense storage system 135 enables the synthesized DNA sequence to be stored and subsequently accessed. In an example, any storage medium capable of storing DNA-based data may be used as the dense storage system 135.

Once the DNA sequence has been stored, it may be subsequently accessed and prepared for sequencing (e.g., being read). As part of the preparation process, multiple copies of the DNA sequence may be generated. In an example, an amplification system 115 of the data storage system 100 may ensure that multiple copies of the DNA data are generated.

A sequencing system 120 may then be used to read DNA sequences from the dense storage system 135. In an example, the sequencing system 120 determines and/or identifies an order of the DNA symbols (e.g., ACTG) in a DNA segment of a DNA sequence that is being read. The sequencing system 120 may use a variety of sequencing methods such as, for example, sequencing by synthesis, nanopore sequencing, and the like.

Once the DNA sequence has been read, a decoding system 125 maps the DNA symbols (e.g., in base-4) back to digital data (e.g., in base-2). For example, in "direct decoding," if the decoding system 125 receives CATGCA as the DNA sequence, the decoding process performed by the decoding system 125 would return 010010110100 (e.g., using the corollary of the binary-to-quaternary mappings discussed above) to a requesting computing device (e.g., computing device 150). Other more complex decoding processes are described herein. In some examples, the inverse of the encoding process used to make the DNA sequence may be used as the decoding process.

In some examples, errors may occur during the synthesis process, the storage process and/or the sequencing process. These errors may be, for example, insertion and deletion ("indel") errors and/or substitution errors. For example, during a synthesis process in which the DNA sequence CATGCA is being synthesized, one or more symbols may be deleted or lost during the creation of the DNA molecule. As a result, a DNA sequence CTGCA may be stored by the dense storage system 135. In another example, during a synthesis process in which the DNA sequence CATGCA is being synthesized, an additional symbol may be added. As a result, a DNA sequence CCATGCA may be stored by the dense storage system 135. Although a single insertion error and a single deletion error are discussed, multiple deletions and/or insertions may occur in a synthesis process. Additionally, these errors may occur during storage and/or during a sequencing process (e.g., during the writing/creating of the DNA molecule, or during the reading/sequencing of the DNA molecule).

In yet another example, during a synthesis process in which the DNA sequence CATGCA is being synthesized, the synthesis system 110 may substitute one symbol for another. As a result, a DNA sequence TATGCA may be stored in the dense storage system 135 instead of the DNA sequence CATGCA. In an example, multiple substitution errors (along with one or more indel errors) may occur during the synthesis process, during storage and/or during a sequencing process.

In order to address the above, the data storage system 100 may include an error correction system 130. The error correction system 130 may be part of the decoding system 125. The error correction system 130 may use various processes to detect and address indel errors and/or substitution errors. In one example, indel errors may be addressed by generating multiple copies of a particular DNA sequence. Once generated, each of the copies of the DNA sequence are read and compared to generate a consensus codeword. For example, a first DNA symbol (or DNA segment consisting of multiple DNA symbols) of a first DNA sequence is compared with a first DNA symbol (or DNA segment consisting of multiple DNA symbols) from one or more of the copies of the DNA sequence. This process repeats for each DNA symbol (or DNA segment) in the DNA sequence.

The error correction system 130 may then determine, based on consensus data across all of the copies, which DNA symbol is the correct (or most correct) DNA symbol for that particular index (or DNA segment). For example, the most prominent DNA symbol in each index of the DNA sequence may be selected as the correct DNA symbol and a consensus codeword is generated for each DNA segment. The resulting consensus codeword is mapped to corresponding ones and zeros and is provided to the decoding system 125 (e.g., a low-density parity check (LDPC) decoder).

In an example, the consensus data generated by the error correction system 130 may be referred to herein as hard bit data or hard information. The error correction system 130 and/or the decoding system 125 described in the present application may also generate and use soft-bit data or soft information using information associated with the consensus data (or using information that is obtained while the consensus data is determined).

For example, once multiple copies of a particular DNA sequence have been copied or otherwise generated (e.g., by the amplification system 115), each copy of the DNA sequence that is associated with a received codeword (e.g., DNA-based data that is to be read from the dense storage system 135), is divided into k DNA segments (where k is equal to or greater than two). Each DNA segment has a DNA segment length n (where n is equal to or greater than one).

For example, the DNA sequence CATGCA may be divided into two different DNA segments having a length of three. As such, a first DNA segment may be "CAT" and a second DNA segment may be "GCA". In another example, the DNA sequence CATGCA may be divided into three different DNA segments having a length of two. In this example, the first DNA segment would be "CA", the second DNA segment would be "TG" and the third DNA segment would be "CA". In yet another example, the DNA sequence CATGCA may be divided into six different DNA segments having a length of one. In this example, the first DNA segment would be "C", the second DNA segment would be "A", the third DNA segment would be "T", the fourth DNA segment would be "G" and so on. The position of each DNA symbol in each DNA segment is referred to as an index. Thus, in the DNA segment "CAT", "C" is the first index, "A" is the second index and "T" is the third index.

The data storage system 100 may also include a dense storage management system 140. In an example, the dense storage management system 140 controls the various operations and/or processes that are carried out by and/or on the dense storage system 135. The operations and/or processes may include the mechanics of storage and retrieval of the DNA data and/or information storage management (e.g., making copies of data, deleting data, selecting subsets of the data, etc.).

The data storage system 100 may also include a control system 145. The control system 145 may include at least one processor, at least one controller and/or other such control circuitry. The control system 145 may include circuitry for executing instructions from the computing device 150 (or from another source) and/or providing instructions to the various subsystems of the data storage system 100.

This process of converting the input data (base-2) into DNA molecule(s) (base-4) and subsequently converting the DNA molecule(s) (base-4) into output data (base-2), including any of the interim processes that the data and/or DNA molecules undergo, may be referred to herein as "the DNA storage channel." It should be understood that, in these examples, it is an objective of the DNA storage channel and the systems and methods described herein to generate output data that is as close to identical to the input data as possible.

Figure 2:
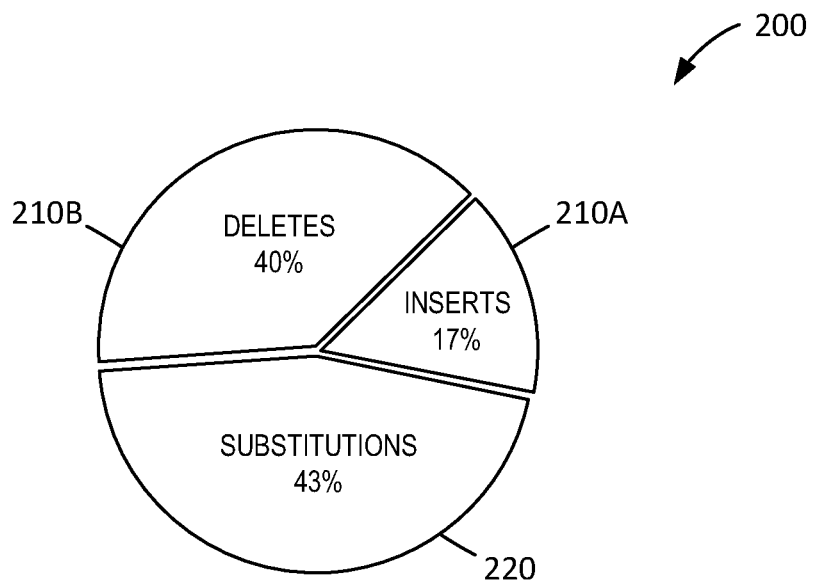
FIG. 2 is an example graph that illustrates some types of errors that can occur in a DNA storage channel.

FIG. 2 is an example graph 200 that illustrates some types of errors that can occur in a DNA storage channel. In the example, the graph 200 illustrates three types of errors that can occur during storage and retrieval (e.g., during synthesis of DNA molecules and the corresponding sequencing of those molecules), as well as an example error percentage for each, as is typical with some known synthesis and sequencing technologies. Each of these error types is presumed to occur sometime during or between synthesis of a particular DNA molecule and a subsequent sequencing of that DNA molecule. For purposes of these examples, it is presumed that the synthesis process for the example DNA molecule started with some string of data in the form of a sequence of base pairs (e.g., of a particular length), that "original data" was accurate (e.g., error-free) when provided for synthesis (e.g., to the synthesis system 110 of FIG. 1), and was used as the source data when generating the DNA molecule. Further, upon sequencing of that DNA molecule, an "output sequence" or "sequenced data" is generated (e.g., by the sequencing system 120 of FIG. 1), and that output sequence is initially identified as a string in the form of a sequence of bases. When the synthesis and sequencing process is error-free, the output sequence data is presumed to be the same as the input sequence data. Further, it should be understood for purposes of these examples that, when an error occurs during either or both the synthesis and sequencing processes, it is immaterial as to which of those two processes caused the error, but merely that the resulting output sequence has the example error.

Three main types of errors are illustrated as possible during the example synthesis and sequencing operation, each of which can cause some changes between the input sequence data prior to synthesis and what is generated as the output sequence data after sequencing the DNA molecule. Insertion errors (or just "inserts") 210A are errors where an additional base is erroneously inserted into the output sequence data. For example, presume a snippet of input sequence data is " . . . ATGCAG . . . ." An insertion error may change this snippet to an output snippet of " . . . ATTGCAG . . . ," where there is a second "T" base erroneously added after the first "T" base. Deletion errors (or just "deletes") 210B are errors where a base is erroneously removed from the output sequence data. Consider the same example snipped of input sequence data " . . . ATGCAG . . . ," but a deletion error causes the output snippet to become " . . . AGCAG . . . ," where the "T" base has been erroneously deleted (e.g., not recreated from during the sequencing process). Substitution errors (or just "substitutions" or "subs") 220 are errors where one base (e.g., in a given position of the snippet) is changed to another base. For example, consider the snippet of input sequence data being " . . . ATGCAG . . . ." A substitution error may change this snippet to an output snippet of " . . . ATGTAG . . . ," where the "C" base has been erroneously changed to a "T" base.

In this example, when one of these three types of errors occurs during synthesis and sequencing, approximately 17% of the errors are inserts 210A, approximately 40% of the errors are deletes 210B, and approximately 43% of the errors are substitutions 220. It should be noted that a particular substitution error 220 changes the value of one base (e.g., in a single position of the DNA sequence), and thus may change one or two bits of the resulting output data (e.g., depending on how the quaternary bases are coded to binary). Substitution errors 220, thus, may corrupt a single byte of output data (e.g., at the site of the error within the output sequence), but such errors are localized and may not otherwise negatively impact the decoding of the other output data.

In contrast, insertion errors 210A and deletion errors 210B can cause errors that extend beyond the region of the error. In an insert 210A, for example, a base is erroneously added to the output string, and all of the bases to the right of the site of the error (e.g., from the right of the erroneously inserted base) are shifted to the right by one position. This can effectively result in a bit-wise shift of one or two bits to the right (e.g., in a binary representation of the output data, and depending on coding). Further, additional erroneous data is injected into the output data (e.g., the one or two bit value of the erroneously inserted base). In a delete 210B, a base is erroneously removed from the output string (e.g., as compared to expectations of the input string), and all of the bases to the right of the site of the error are effectively shifted to the left by one position. This can also result in a bit-wise shift of one or two bits, but to the left. Further, the one or two bits of data represented by the erroneously removed base is lost.

As inserts 210A and deletes 210B result in similar problems during decoding and recreation of the source data (e.g., namely, shifting the output data either to the right or to the left), these are collectively referred to herein together as "indel" errors (or just "indels") 210.

Figure 3:
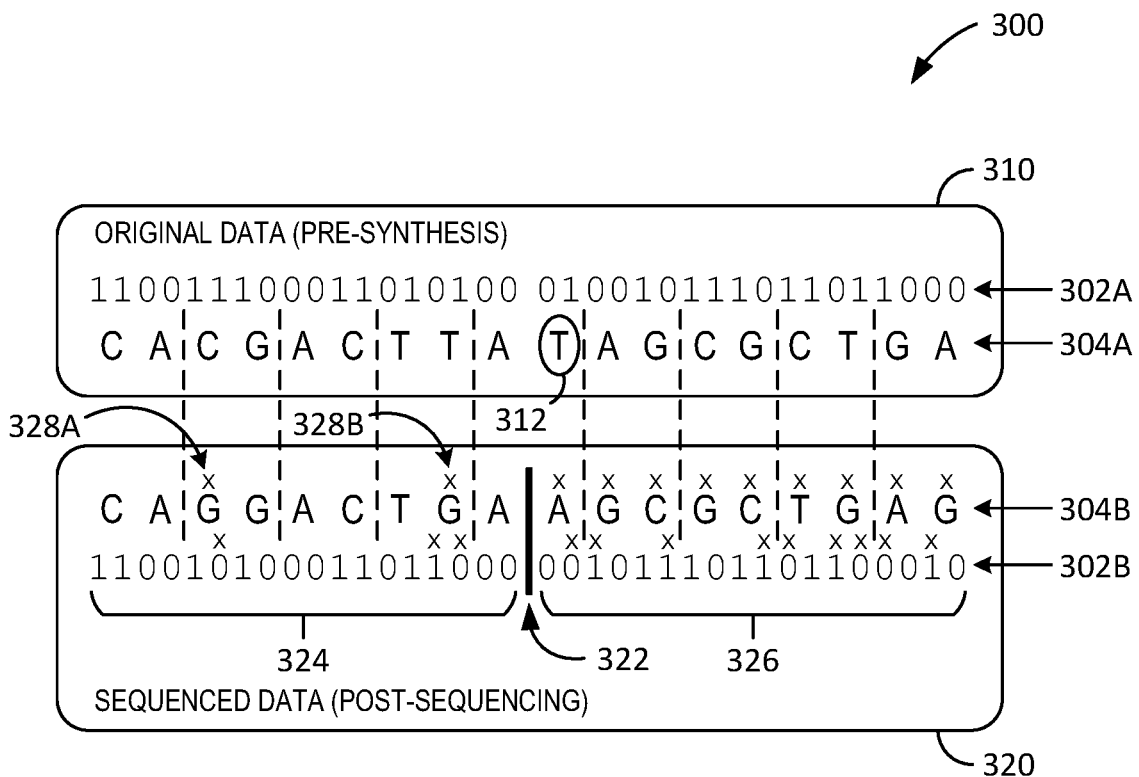
FIG. 3 is a diagram of an example indel error.

FIG. 3 is a diagram 300 of an example indel error 210. In this example, for purposes of illustrating the indel error 210, a snippet of original data 310 is shown above a snippet of sequenced data 320, and these data 310, 320 are aligned and interpreted sequentially left to right. The original data 310 includes both a binary representation of source data in the form of a bit string 302A, as well as a quaternary, base-4 representation of a base string 304A (e.g., in the four DNA bases, A. T. G, and C). The bases of the base strings 304A, 304B are vertically aligned so as to highlight the expected relative position of the output bases 304B relative to the order of the input bases 304A (e.g., as illustrated by periodic vertical broken lines). It is presumed, in this example, that a simple encoding of bases with binary is used: A=00, T=01, G=10, and C=11. However, it should be noted that other encodings are possible.

The original data 310, in this example, is an ordered sequence of 18 bases long (e.g., 36 bits). Further, it is presumed that the original data 310 is a snippet of input data that is used to synthesize a DNA molecule (e.g., as encoded by the encoding system 105), and that this may only be a portion of the input data. The sequenced data 320 represents a snippet of output data as it was generated from the DNA molecule during sequencing. The sequenced data 320 also shows 18 bases (e.g., 36 bits), but more output data may also be present (e.g., to the right or left of the bases shown). The sequenced data 320 also includes both a quaternary, base-4 representation of a base string 304B (e.g., in the four DNA bases, A. T. G, and C), as well as a binary representation of the sequenced data 320 in the form of a bit string 302B.

In this example, two substitution errors 220 are illustrated in a left portion 324 of the sequenced data 320, each of which are illustrated with an "x" over their respective substituted bases 328A, 328B in the base string 304B. More specifically, in the first substitution error 220, a "C" base was recreated at as a "G" base 328A, causing what was intended to be a "11" (binary) from the binary string 312A of the original data 310 to be changed to a "10" in the binary string 312B of the sequenced data 320 (also illustrated with an "x" over the changed bit in the binary string 312B). Similarly, in the second substitution error 220, a "T" base was recreated as a "G" base 328B, causing a "01" to be changed to a "10" in the binary string 312B of the sequenced data 320 (where each of the two changed bits includes an "x" over the changed bits). It should be noted that, while these substitution errors 220 do introduce a corruption in one or two of the bits of the data, the occurrences of these substitution errors 220 do not necessarily impact the integrity of neighboring or subsequent data in the sequenced data 320. For example, after the first substitution error of the substituted base 328A, the next four bases are correctly "GACT" until the second substitution error base 328B. Since substitution errors do not include a shift in alignment, the impact of substitution errors is limited to the one or two bits data that the substituted base 328 represents. Further, such substitution errors 220 can be corrected by other methods, such as error correction techniques provided by the error correction system 130 using parity information included in the DNA molecule.

In this example, FIG. 3 also illustrates an indel error 210, which causes more widespread problems in the sequenced data 320. Here, a "delete" type error 210B has occurred. More specifically, a "T" base 312 that was present in the original data 310 does not appear at its proper position in the sequenced data 320. Since this "T" base 312 has not been properly recreated in the sequenced data 320, all of the bases to the right of the deleted base 312 now have been shifted to the left by one base position. A skew point 322 is shown in FIG. 3 to illustrate where this indel error 210 occurred. The skew point 322 represents where, in the sequenced data 320, the indel error 220 begins to impact the sequenced data 320. More specifically, the integrity of the data 324 to the left of the skew point 322 is not directly impacted by this example indel error 220, but data 326 to the right of the skew point 322 is significantly impacted (e.g., due to the shift in alignment from the missing base 312).

The impact of this example delete error 210B is illustrated in FIG. 3 to show an "x" over each base in the base string 304B that does not properly match the associated base from the base string 304A of the original data 310. Here, this delete error 210B causes all of the bases of the data 326 to the right of the skew point 322 to not match (e.g., a 100% base error rate in this short snippet). Further, FIG. 3 also similarly illustrates which bits of the sequenced bit string 302B do not properly match their counterpart bit positions of the bit string 302A of the original data 310 (e.g., with an "x" over each mismatched bit).

This example includes nine bit errors in the data 326 after (e.g., to the right of) the skew point 322, resulting in a bit error rate of 9 bit mismatches/18 bits=50% in this short snippet. In contrast, the bit error rate prior to (e.g., to the left of) the skew point 322 is 3 bit mismatches/18 bits=16.7%. As such, the impact of a delete type error 210B is evident. Not only is some data lost (e.g., the missing "T" base 312 and its associated bits are gone), but the absence of the missing base 312 also causes a shift in subsequent bases in the sequenced data 320 that dramatically impacts data alignment and mismatches in subsequent data 326 past the skew point 322. While the example shown here illustrates a delete error 210B, it should be apparent that an insert error 210A would exhibit very similar effects (e.g., causing extra data to be injected at the skew point 322, and a similar alignment shift but to the right).

Figure 4:
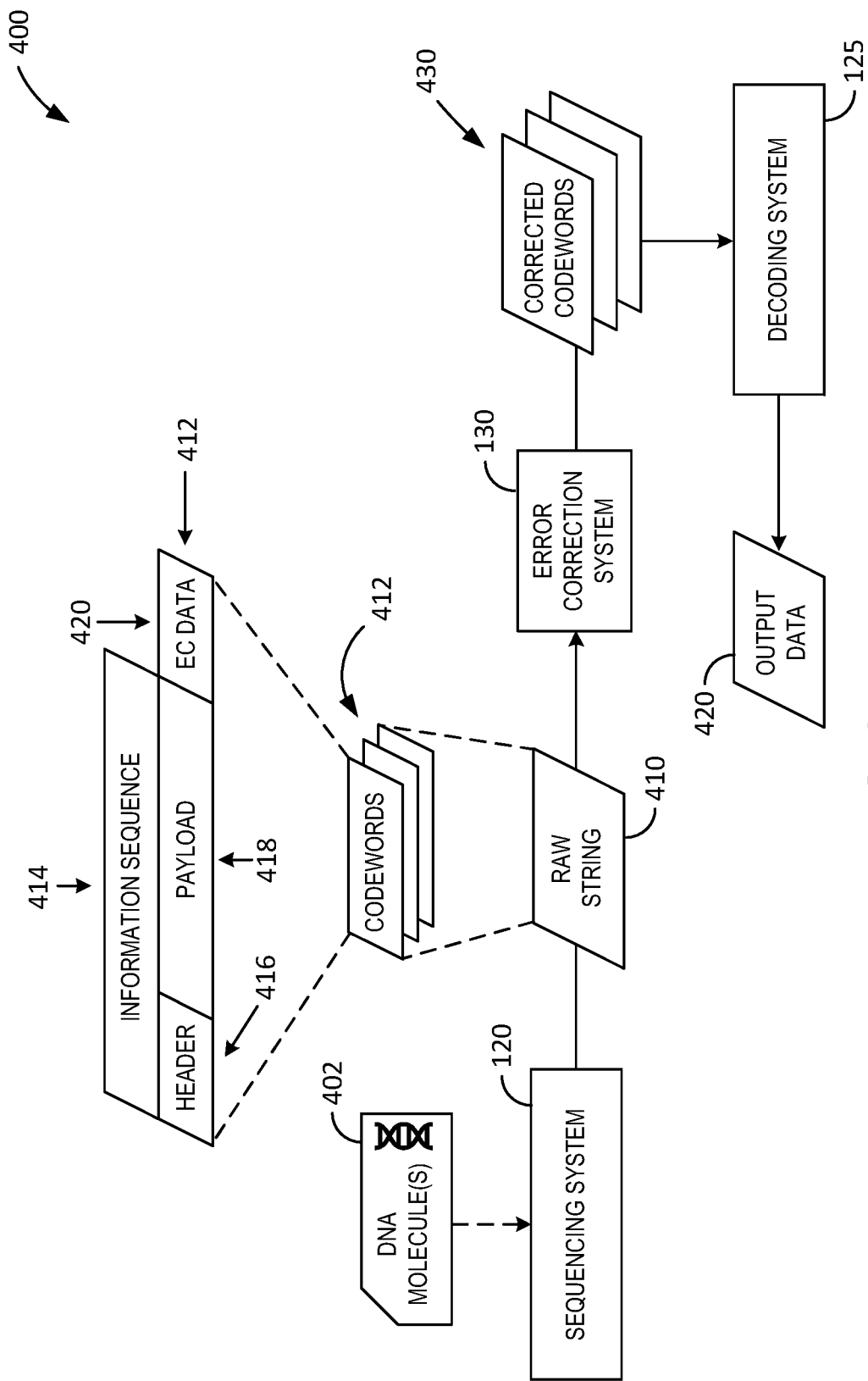
FIG. 4 is an architecture and data flow diagram of components of a DNA storage system that is configured to perform aspects of error correction for indel type errors on data generated from the sequencing of DNA molecules.

FIG. 4 is an architecture and data flow diagram of components of a DNA storage system that is configured to perform aspects of error correction for indel type errors on data generated from the sequencing of DNA molecules 402. In some examples, aspects of the DNA storage system 400 are similar to the DNA storage system 100 and the DNA storage subsystem 102 shown in FIG. 1. In this example, a DNA molecule 402 is sequenced by the sequencing system 120 to generate a "raw string" 410 of data (e.g., a sequence of DNA bases as embodied in the DNA molecule 402). The raw string 410, or portions thereof, may be similar to the sequenced data 320 shown in FIG. 3, and may be subject to indel type errors as described.

In the example, the raw string 410 includes one or more codewords 412, where each codeword 412 includes a sequence of "raw data" in DNA bases generated from the DNA sequencing. Each codeword 412 includes at least a payload segment (or just "payload") 418 and may additionally include a header segment (or just "header") 416 and an EC data segment (or just "EC data") 420. In this example, the payload 418 represents data that is the subject of this DNA storage (e.g., "user data," or a portion thereof, that is meant to be stored in DNA molecule(s) 402), where the header 416 and EC data 420 are ancillary data or metadata used by this DNA storage channel to various effects. For example, the header 416 may have a standard information format and may include information about the payload 418 such as, for example, a description of the type of content in the payload 418, the source of the payload 418 (e.g., a unique identifier shared amongst sibling payloads used during reassembly), sequencing information for this particular payload (e.g., where, amongst its sibling payloads, this particular payload 418 belongs), or the like. EC data 420 may include data used for error correction, such as error correction codes, parity data, or the like. Various error correction techniques for NAND storage are described in U.S. Pat. No. 10,725,860 to Avraham et al., which is hereby incorporated by reference in its entirety, any of which may be incorporated into the error correction functionalities described herein. In this example, the header 416 and payload 418 are also referred to herein as an "information sequence" 414 of the codeword, as the information sequence 414 is the subject of the EC data 420. In other words, the EC data 420 is used to perform error correction on both the header 416 and the payload 418.

The error correction system 130 performs various error correction functionalities on the raw string 410 and the associated codewords 412. More specifically, in these examples, the error correction system 130 corrects indel errors 210 occurring within the codewords. FIG. 5 to FIG. 9 illustrate various methods for correcting such indel errors 210. In some examples, the error correction system 130 may also perform other error correction techniques on the codewords 412 (e.g., using the EC data 420), typically after the described indel error correction is performed, as the presence of unaddressed indel errors and the associated bit error rate may be too significant for the other ECC techniques to properly function. Upon performing these various error corrections, the error correction system 130 outputs corrected codewords 430 that are subsequently decoded by the decoding system 125 to generate output data 420 (e.g., as binary data, representing the subject user data encapsulated in the DNA molecule(s) 402.

Figure 5:
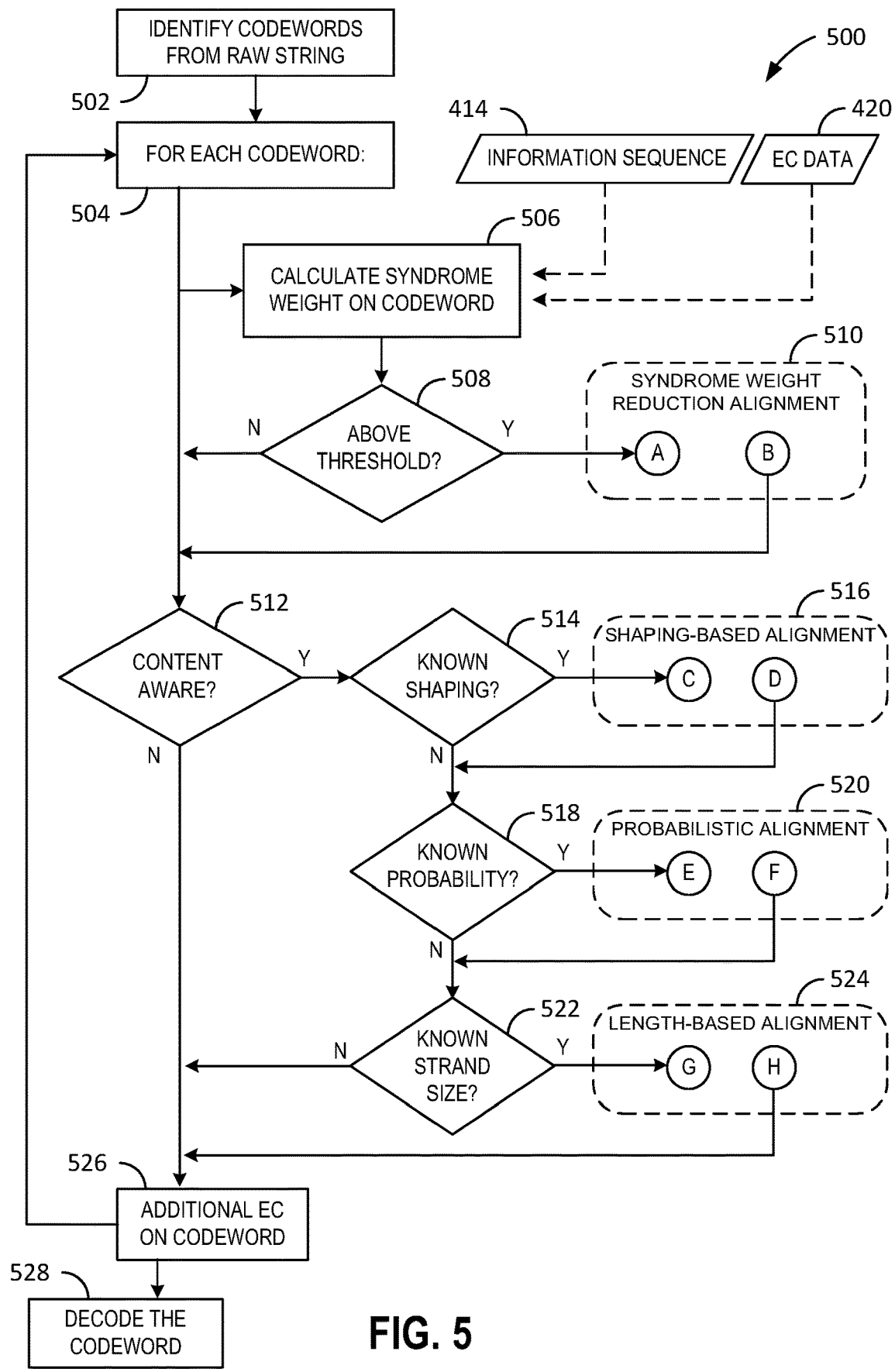
FIG. 5 is a flow chart of an example method for correcting indel errors in the codewords of FIG. 4.

FIG. 5 is a flow chart of an example method 500 for correcting indel errors 210 in the codewords 412 of FIG. 4. In some examples, the method 500 may be performed by the error correction system 130 after the DNA molecule(s) 402 are sequenced and the raw string 410 is provided by the sequencing system 120. In this example, the method 500 may perform any one or more of four techniques for dealing with indel errors 210. While the ordering of these indel remediation techniques is illustrated in an example order in FIG. 5, and that all four techniques are illustrated in the example as an integrated, ordered, and multifaceted approach, it should be understood that other combinations and ordering of any or all of the four techniques are possible.

At operation 502, the error correction system 130 identifies codewords 412 from the raw string 410. At loop operation 504, the error correction system 130 performs indel remediation on each of the codewords 412 individually. In the example, these indel remediations are performed on the entirety of the information sequence 414 (e.g., the header 416 and the payload 418) and using the EC data of the codeword 412. In other examples, these indel remediations may be performed on just the header 416 and/or the payload 418. As such, the information sequence 414 represents a sequence of bases that is under inspection for the presence of indel errors 210, and thus may be subject to correction.

In the example, the first indel remediation performed on a particular codeword 412 is referred to herein as "syndrome weight reduction alignment." More specifically, at operation 506, the error correction system 130 calculates a syndrome weight for the information sequence 414 of the current codeword 412. Syndrome weight is a measure of how well the information sequence 414 matches the EC data 420 (e.g., how many parity equations are satisfied), where a higher syndrome weight indicates a higher number of errors in the information sequence 414 or a greater discrepancy between the EC data 420 and the information sequence 414.

At operation 508, the error correction system 130 tests whether the computed syndrome weight is above a predetermined threshold (or "syndrome weight threshold"). If the syndrome weight of this codeword is higher than the syndrome weight threshold, then it is considered likely that there are one or more indel errors present in the codeword 412. As such, the error correction system 130 branches to a syndrome weight reduction alignment subprocess 510. If the syndrome weight of this codeword 412 is not above the threshold, then the indel remediation method 500 continues down to operation 512. The syndrome weight reduction alignment subprocess 510 is described in greater detail with regard to FIG. 6.

At operation 512 in the example, the method 500 determines whether certain features of the codeword are known. The error correction system 130 may be configured to search for and identify indel errors 210 based on such known features. For example, at operation 514, the error correction system 130 determines whether the codeword 412 was encoded with shaping data. The input data for some DNA molecules 402 may undergo an encoding process (e.g., by the encoding system 105) prior to synthesis. This encoding process may, for example, perform a mapping of fragments of the input data, thereby changing or "shaping" each unique fragment (e.g., a unique sequence of 3 bases) to a different fragment (e.g., a unique sequence of 4 or more bases). Or in another example, two of the four DNA bases may be mapped to binary 0 and the other two DNA bases may be mapped to binary 1, and the encoding process may alternate between the two bases of a given binary digit when repeating that digit (e.g., so as to avoid adjacent symbols, which can increase error levels in the DNA channel). Such encodings may be performed to, for example, avoid certain base combinations or other sequences that are known to be more error prone. As such, the error correction system 130 may use this encoding data to both detect the presence of potential indel errors as well as identify approximately where those indel errors may be within the information sequence 414. In some examples, this encoding data may be stored in a conventional database and may be identified and referenced by, for example, an association between the encoding data and a unique identifier associated with the DNA molecule 402 (e.g., perhaps included in the header 416). Various shaping/encoding techniques for DNA storage are described in U.S. Provisional Patent Application No. 63/429,208 to Zamir et al., which is hereby incorporated by reference in its entirety, any of which may be incorporated into the error correction functionalities described herein.

If, at operation 514, the error correction system 130 determines that there is known shaping data associated with this codeword 412, then the error correction system 130 performs a shaping-based alignment subprocess 516 on the codeword 412. Shaping-based alignment is described in greater detail below with respect to FIG. 7.

At operation 518 in the example, the method 500 determines whether there is known probability data associated with the codeword 412 and may perform a "probabilistic alignment" using such data. For example, the error correction system 130 may maintain a database of probabilities for various sequences that are determined to be less likely (e.g., historically low probability occurrences in typical data or, additionally or alternatively, historically high indel probability sequences from past detected indels). With such data, if a low probability original sequence or high indel probability sequence occurs within the information sequence 414, that localized region may be marked as suspect and may be inspected for potential indel occurrences. If, at operation 518, the error correction system 130 determines that there is known probability data that may be used to detect indels 210, then the error correction system 130 performs a probabilistic alignment subprocess 520 on the codeword 412. Probabilistic alignment is described in greater detail below with respect to FIG. 8.

At operation 522 in the example, the method 500 determines whether there is a known size data (e.g., a known strand size) associated with the codeword 412 and may perform a "size-based alignment" based on such knowledge. For example, there may be an expected size for the information sequence (e.g., in a predetermined number of bases). As such, this size data can be used to identify at least a ratio of insert errors 210A to deletion errors 210B within the information sequence 414. If, for example, the information sequence 414 has an expected size of 200 bases but this particular information sequence 414 only contains 198 bases, then there are two more delete errors 210B than insert errors 210A (e.g., two deletes 210B with no inserts 210A, three deletes 210B with one insert 210A, and so forth). If, at operation 522, there is size data known for the codeword 412, then the error correction system 130 may perform a length-based alignment subprocess 524 on the codeword 412. Length-based alignment is described in greater detail below with respect to FIG. 9.

Upon detection and correction of the indel errors 210 of the codeword 412, the error correction system 130 proceeds to perform additional error correction on the codeword 412 at operation 526. Such additional error correction may include, for example, correction of substitution errors (e.g., using parity information in the EC data and/or using initial state transition probabilities).

For example, during a decoding process, the error correction system 130 may use initial state transition probabilities to address various substitution errors. Additionally, the initial state transition probabilities may be adjusted in real time or substantially real time. For example, the error correction system 130 may update the initial state transition probabilities based, at least in part, on information obtained or determined during various iterations of a decoding process. This process is described in more detail in U.S. Provisional Patent Application No. 63/428,643 to Avraham et al., entitled Calibrating State Transition Probabilities Associated with a DNA-Based Storage System to Optimize Decoding, filed 29 Nov. 2022, which is hereby incorporated by reference in its entirety.

Emerging from operation 526, the information sequence 414 has been corrected for indel errors 210 and/or substitution errors 220, and thus should be free of at least those types of errors. In any of the above indel remediation operations, the codeword 412 may have been updated when an indel error 210 was detected. In some examples, the method 500 may include checking the syndrome weight of the current codeword before determining to proceed on (e.g., returning to any of the various alignment techniques described herein if the syndrome weight is below a threshold). At operation 528 in the example, the corrected codeword 412 may be passed as a corrected codeword 430 to the decoding system 125 and decoded. Further, the method 500 may loop to operation 504 to perform indel remediation operations on the next codeword 412.

In distinguishing differences between NAND-type storage channels with DNA-type storage channels, it should be noted that NAND error correction typically uses binary-based (base-2) error correction techniques, where in DNA-type storage channels, error correction techniques may be used at either the base-4 level (e.g., based on the string of nucleotide bases representation) or on a binary conversion of those nucleotide bases. Further, in NAND-type storage, indel type errors are typically quite rare, and thus may be addressed in different ways, or may not be addressed at all (e.g., the data may either be taken from another location or the operation just fails), where in DNA-type storage, indel type errors may be the majority of errors, and thus an alignment solution to address indel errors plays a much more significant role in error correction, and may even allow changes in the way the data is encoded to allow for better synchronization. Further, in DNA-type storage, the shaping and known probabilities are related to physical attributes of the DNA, and its error patterns may be derived by the physical behavior and the conditions introduced by the DNA. Such probabilities may include, for example, the transitions between states and the chances to get long repetitions. Shaping is similar to probabilities as it also comes in many cases to mitigate such repetitions, hence knowing such gives some hard boundaries and concrete indications of malformed data. Moreover, in NAND memory, a data sampling size is determined by a physical size of the memory, and thus will always be of the same length (e.g., construed by physical dimension). Some data may be missing, in which case the missing part will hold whatever data may reside in the physical media at that time, or some data may be added, in which case some data will not have any physical media to store it in, and thus may be lost. In the case of DNA-type storage, insertions and deletions mean one or more nucleotides were added or deleted, and thus the data length will physically change giving a strand size that may be different than the original data strand size.

In some examples, DNA encoding may place known data ("markers", e.g., a specific sequence of bases) in known locations to allow for better synchronization. For example, some markers may be placed at various known locations within codewords and those marker locations can be used to determine whether indel errors are present (e.g., before each of the respected marker locations), thus allowing the alignment processes to focus only on sections of the codeword that are identified, by a corrupted markers, to have one or more indels. For example, presume a codeword is configured with three such markers that are separated within the codeword, and are thus expected at those known locations. As such, if the first marker is intact (e.g., the expected sequence of bases appears at the expected location of the codeword), then it may be presumed that, for example, there are no indel errors prior to the marker, or that the number of insert errors before the marker is equal to the number of delete errors before the marker.

Figure 6:
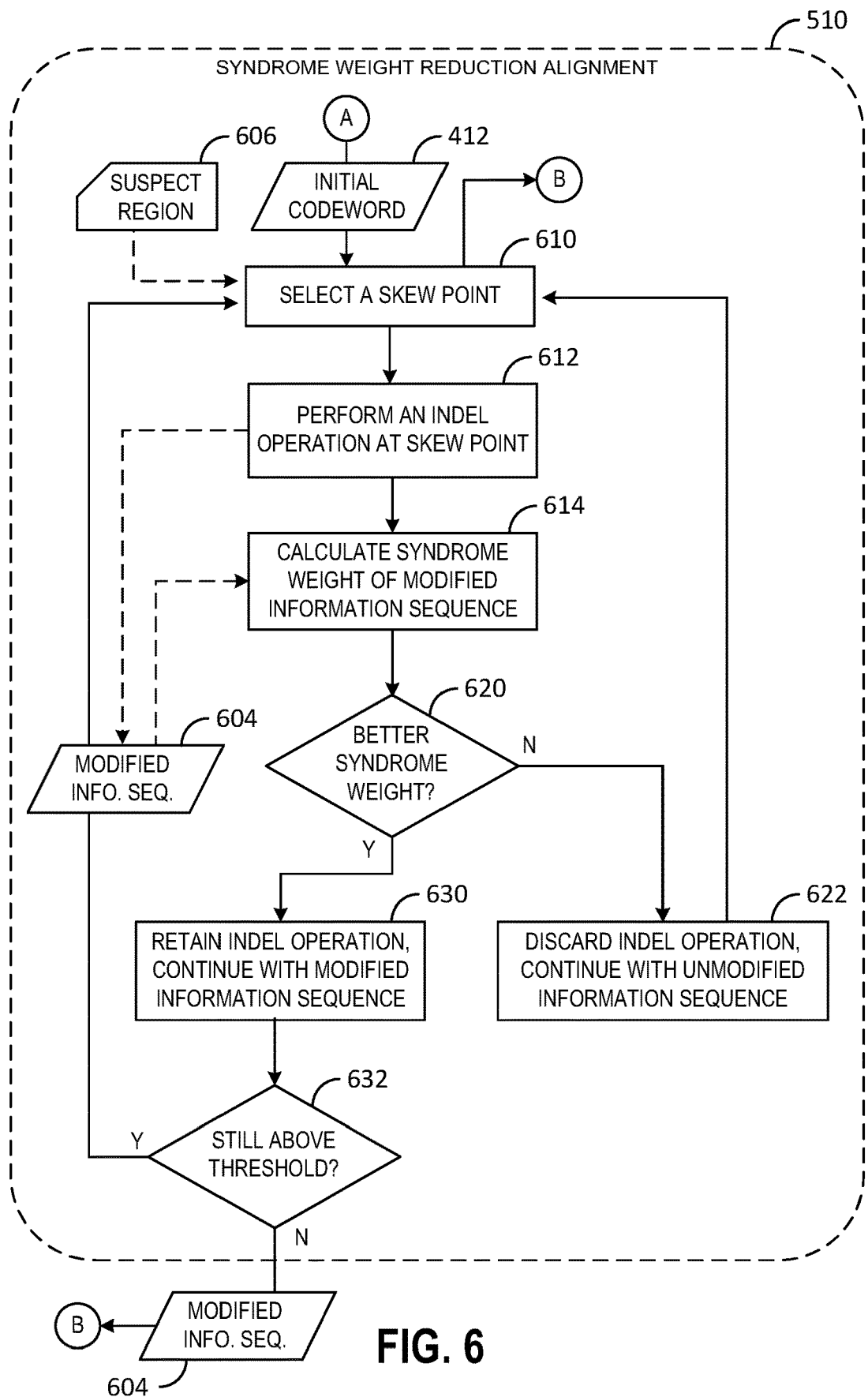
FIG. 6 is a flow chart illustrating the syndrome weight reduction alignment subprocess shown in FIG. 5.

FIG. 6 is a flow chart illustrating the syndrome weight reduction alignment subprocess 510 shown in FIG. 5. In this example, the subprocess 510 begins with an initial codeword 412, including EC data 420 and an initial information sequence 414 that may be modified during this subprocess 510. Further, the syndrome weight computations and parity-check equations described herein are presumed to be performed on the binary representation/decoding of the information sequence 414 (e.g., the bit string 302B of the sequenced data 320 of the codeword 412), while the indel operations may be performed on the DNA-base representation of the codeword 412 (e.g., the base string 304B of the sequenced data 320 of the codeword 412).

An error-free codeword 412 is a codeword 412 in which all parity-check equations provided by the EC data 420 and the associated error checking equations are satisfied. In such error-free situations, the syndrome weight for the error-free codeword 412 is zero. When the codeword 412 has one or more errors (an "EC-deficient" codeword), the syndrome weight will be a positive (e.g., non-zero) value. There is a correlation between the number of bit flips in the codeword 412 and the syndrome weight value. High syndrome weight corresponds to a high number of bit flips while low syndrome weight corresponds to a low number of bit flips. Calculation of the syndrome weight is considerably faster and simpler than decoding the data and thus can be used as a faster means for alignment.

Substitution errors 220 can increase the syndrome weight, as changes to a single base can cause one or more of the parity-check equations to fail. However, as mentioned above, a single substitution error 220 impacts only one or two bits of the codeword 412, and thus only a small number of parity-check equations (e.g., linearly based on the number of bit flips). In contrast, and as illustrated in FIG. 3, the alignment issues caused by an indel error 210 can impact numerous bases after the skew point, and thus can cause a much greater number of parity-check equations to fail. As such, the likely presence of at least one indel error can be identified by a high syndrome weight.

In this example, at operation 610, the error correction system 130 selects a skew point 322 within the information sequence 414 at which to perform an indel operation. In some examples, the error correction system 130 may perform an exhaustive approach of selecting skew points 322, such as starting at the beginning of the information sequence 414 (e.g., before the first base) and continuing with skew points between each subsequent base in subsequent iterations. In some examples, the error correction system 130 may have identified a suspect region 606 of the information sequence 414 (e.g., through other methods described herein) and, as such, the skew point selection at operation 610 may include selecting skew points 322 in or around the suspect region 606 (e.g., starting at an identified base, at each potential skew point 322 within the suspect region 606, or such).

At operation 612, the error correction system 130 also selects which type of indel operation to perform on the information sequence 414 at the skew point 322, as well as other details regarding the indel operation, and performs that indel operation on the information sequence 414 at that skew point 322. The two types of indel operations that may be performed are a base insert and a base delete. These are referred to herein as indel "operations" as they are being intentionally performed on the information sequence 414, and it should be understood that these operations are effectively acting as opposite of and complementary to the insert errors 210A and delete errors 210B of FIG. 2.

For example, an insert operation includes inserting a base into the information sequence 414 at the skew point 322, thus shifting all of the bases to the right of the skew point 322 one base position to the right (e.g., to make room for the newly inserted base). This insert operation would cure at least the alignment problems introduced by a single delete error 210B if that delete error 210B had happened at this particular skew point 322. Similarly, a delete operation includes deleting a base from the information sequence 414 at (e.g., to the right or left of) the skew point 322, thus shifting all of the bases to the right of the deleted base to the left by one position to the left (e.g., to occupy the space of the deleted base). This delete operation would cure the alignment problems introduced by a single insert error 210A if that insert error 210B had happened at this particular skew point 322. While the skew point 322 is illustrated as a space between two bases in FIG. 3, it should be understood that, for insert operations, this is where the inserted base is added, where for delete operations, it is the base to the right of the skew point 322 that is the subject of the delete operation in these examples.

In this example, one of the two indel operations is selected and performed at operation 612 during this iteration. This indel operation generates a modified information sequence 604 that is used during this iteration, and which may be retained if improvement in syndrome weight is seen. In some examples, the error correction system 130 may separately analyze both types of indel operations at this particular skew point 322 (e.g., separately processing an insert operation and a delete operation through the remainder of this loop, or in a separate iteration of this loop).

At operation 614, the error correction system 130 calculates the syndrome weight of the modified information sequence 604. This syndrome weight may be calculated similarly to the calculation of operation 506 in FIG. 5.

At operation 620, the error correction system 130 compares a prior syndrome weight of the information sequence 414 to the calculated syndrome weight of the modified information sequence 604. If this comparison does not indicate any significant improvement in the syndrome weight, then, at operation 622, the error correction system 130 discards this indel operation and continues to another iteration of this subprocess 510 with the unmodified information sequence 414 (e.g., reverting back to the information sequence 414 as it was before this indel operation). If this comparison indicates a significant improvement in the syndrome weight (e.g., a lowering of the syndrome weight, a lowering of the syndrome weight by at least a predetermined amount) then, at operation 630, the error correction system 130 retains this indel operation and continues with the modified information sequence 604. At operation 632, the error correction system 130 compares the current syndrome weight of the modified information sequence 604 against the syndrome weight threshold (e.g., as in operation 508 of FIG. 5) and exits this subprocess 510 if this current syndrome weight is lower than the threshold. This exit may return the modified information sequence 604 to be used by the method 500. If the current syndrome weight is above the threshold, then the error correction system 130 loops back to operation 610 and selects a new skew point 322 and/or indel operation to apply.

In scenarios where an insert operation is applied, the inserted base may be initially selected as one of the four bases. In cases where the skew point 322 is correct (e.g., an actual site of a delete error 320B), then some improvement in the syndrome weight may be expected, as the alignment issue introduced by that one delete error 320B has been cured by this insert operation. However, if the skew point 322 is correct, but the inserted base is not the same as the base that was deleted in the original delete error 320B, then that new base effectively becomes a substitution error 220. In some examples, when an insert operation has been confirmed to improve the syndrome weight at operation 620, the error correction system 130 may apply each of the four bases to the position of that new base, score each of those variations, and select the new base based on which syndrome weight is the lowest. As such, this may avoid leaving a substitution error in the information sequence 414.

In some examples, the iterations of this subprocess 510 may be configured with an escape other than the syndrome weight threshold of operation 632. For example, if all skew points and indel operations have been tried and the syndrome weight threshold remains above the threshold, then the subprocess 510 may exit (e.g., when attempting to select the next skew point at operation 610). Similarly, in scenarios where this subprocess 510 was initiated with a suspect region 606, the subprocess 510 may terminate after each indel operation has been evaluated at all possible skew points 322 within the suspect region 606.

It should be noted that syndrome weight is a good predictor to the bit error rate (BER), and thus the system can estimate if the BER levels will be correctable by the ECC engine when a correction capability is known. For example, presume an EC code can fix BER levels of up to 5% BER. As such, if the syndrome weight shows values exceeding 5% BER, then indel alignment correction may be performed. In some examples, the threshold that will invoke indel alignment may be configured higher in a system that can afford to occasionally fail (e.g., based on use case) and which would benefit from avoiding the overhead of such a calculation, or lower in a system that can afford such calculations but cannot afford failure.

In some examples, multiple codewords may be included in a single DNA strand. As such, indel errors and their associated alignment issues can cause alignment issues in subsequent codewords (e.g., because they share a single strand). Accordingly, alignment corrections made in an earlier codeword may be propagated to subsequent codewords in the shared strand.

Figure 9:
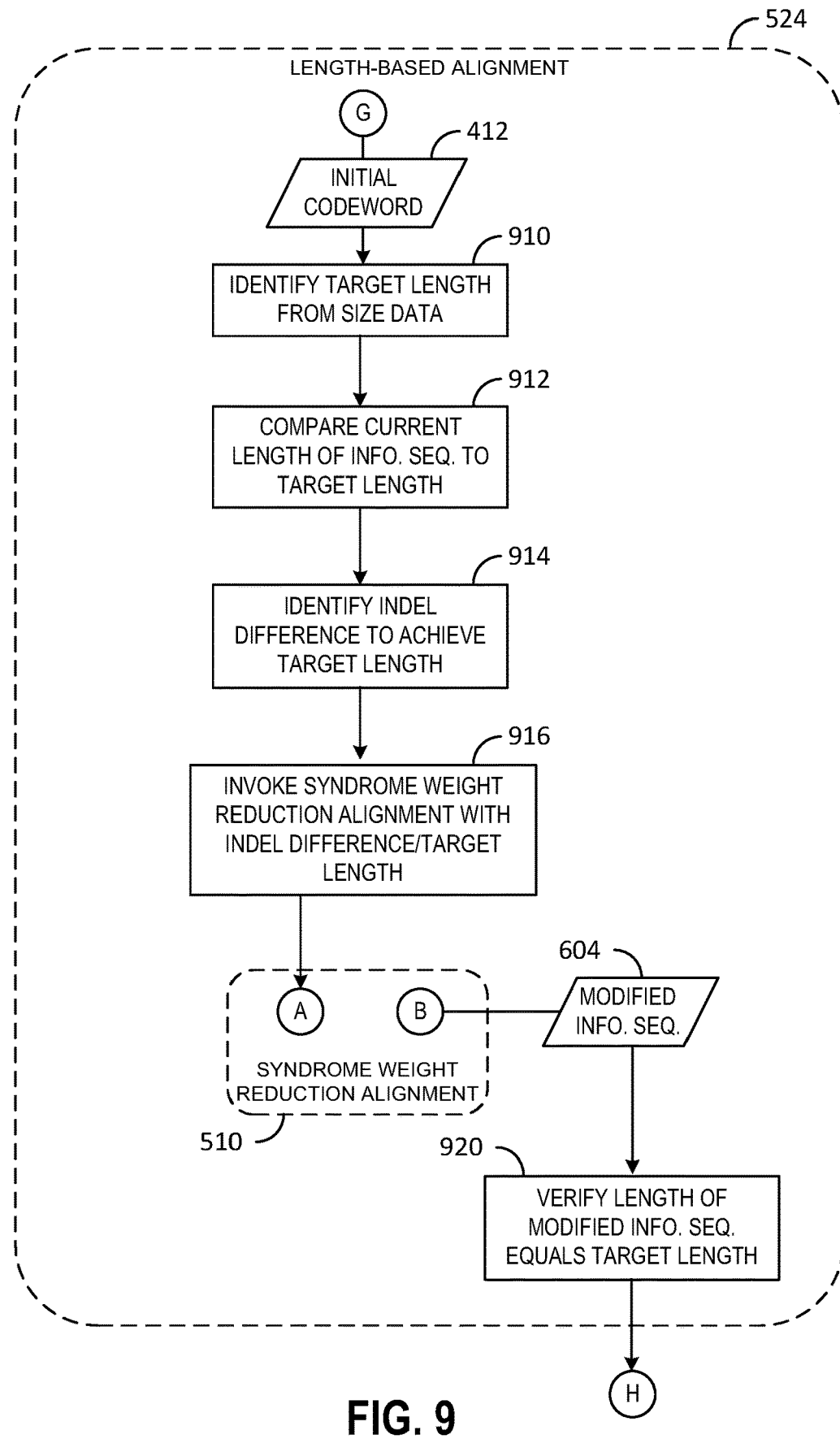
FIG. 9 is a flow chart illustrating the length-based alignment subprocess shown in FIG. 5.

In some examples, aspects of a method 900 that utilize size data, as shown in FIG. 9, may be incorporated into the method 600 of FIG. 6. For example, a known target length for the codeword as compared to a current length of the codeword being inspected may allow this syndrome weight calculation of method 600 to identify how many inserts should be expected relative to the number of deletes.

The example method 600 shown in FIG. 6 describes one process for finding indel errors and their respective locations and correcting those errors. In some examples, indel errors may be identified by an entropy-based method. The data written to storage tends to be non-random, as it may include patterned data structures, journaling, data padding, and the like. Data entropy is a measurement of the amount of disorder found in the data. In this entropy-based method, shifts in data are located by entropy minimization, as the data is typically scrambled, causing misalignment to prevent correct descrambling, thus will create randomized data with high entropy. The data's entropy may be measured by:

$$H(X) = -\sum_{i=1}^{n} P(x_i) \log P(x_i),$$

where $P(x_i)$ is the probability of a symbol to occur in the data stream. Completely random data will have an entropy of 1. As the data shows more order and structure, it will have lower entropy (e.g., in the extreme case of constant data, the entropy will be 0).

Some data may be scrambled before writing to the DNA storage channel. On simple manner of scrambling the data is to xor the data with a pseudo-random sequence which can be generated with a short seed, where the same seed is used to regenerate the sequence and subsequently performing xoring again to descramble the data. Therefore, assuming the data has a pattern to it and that it can be descrambled, the error correction system 130 may perform an iterative process, similar to the syndrome weight process above, in which the scrambled data is moved at some skew point, then the data is descrambled and entropy is checked, comparing it to the entropy of the original noised data. The original noised data should be a mix of patterned data (e.g., up to the indel) and random data (e.g., from the indel onwards) due to the mismatch with the descrambling sequence. Each shift of the data can be viewed as a shift to scrambling sequence in order to place it in the correct alignment with the data, where a fully correct alignment will uncover the full original data, and hence will lower the entropy to a minimal value. Hence, by one sweep of the data (e.g., even with jumps between alignment points, such as trying to move every n'th symbol, and not one by one), indels can be found and corrected.

For example, let the input data be noted as $\overline{D}$ and the function of finding the scrambling seed and its data entropy as EM, the entropy that matches the best seed sequence is given by:

$$H_D = EM(\overline{D}).$$

And let the function that modifies the data at a given location by shifting it left and padding it in the end, or shifting it right and padding, be noted as R:

$$\overline{D_2} = R(\overline{D_1}, \text{location, shift}).$$

As such, the following algorithm is provided to find D', which is the correct data after realignment:

$$\overline{D'} = \overline{D},$$

$$H_{D'} = EM(\overline{D'}),$$

In an outer loop, iterating for each location=start of buffer to end of buffer, and in an inner loop, iterating for each shift in all allowed shifts:

$$\overline{D_{shifted}} = R(\overline{D'}, \text{location, shift});$$

$$H_{D_{shifted}} = EM(\overline{D_{shifted}});$$

if $H_{D_{shifted}} < H_{D'}$, then:

$$\overline{D'} = \overline{D_{shifted}};$$

$$H_{D'} = H_{D_{shifted}};$$

As such, this data entropy minimization technique may be used in conjunction with any of the alignment techniques described herein for indel alignment, in lieu of or in addition to the syndrome weight alignment process.

Figure 7:
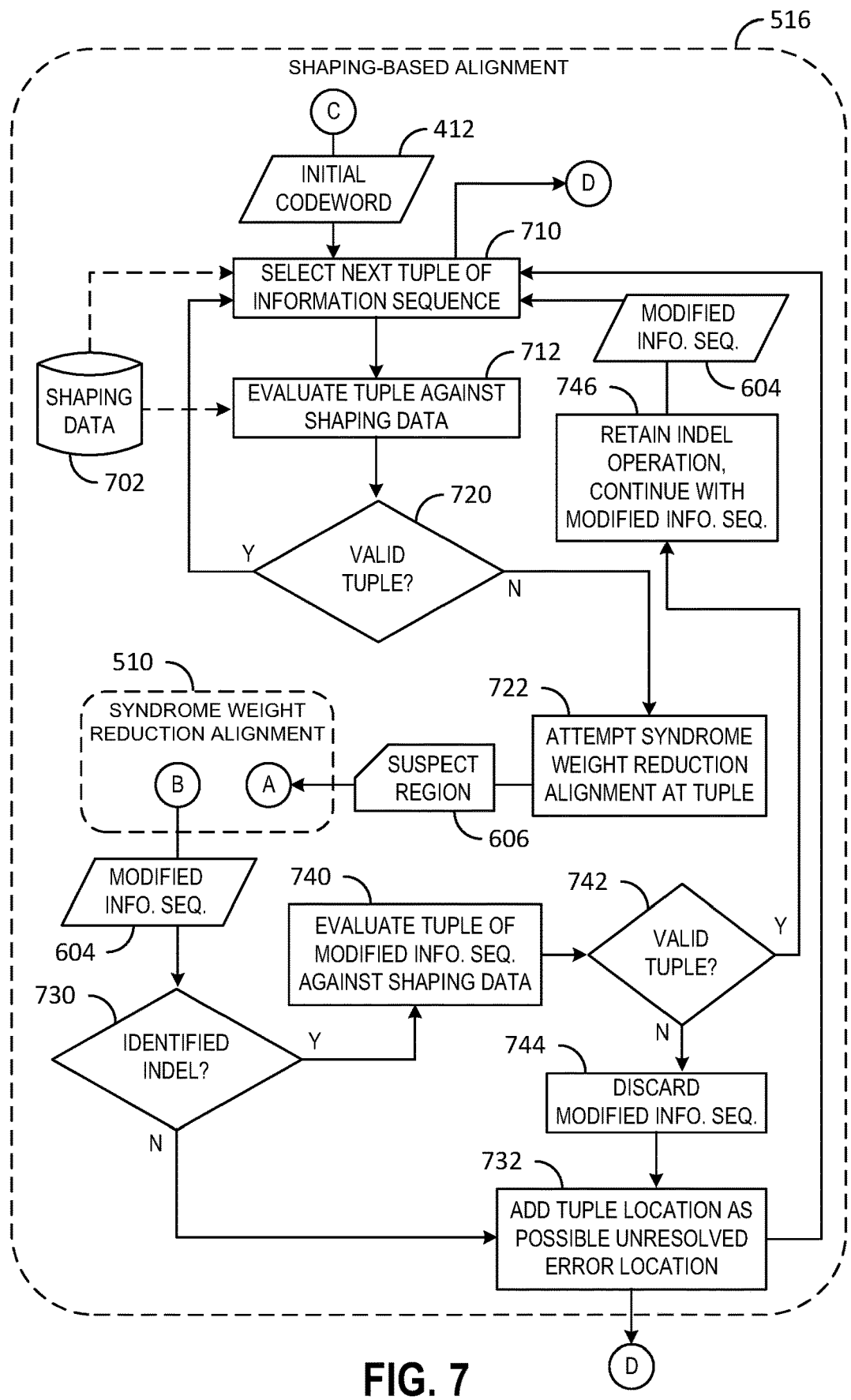
FIG. 7 is a flow chart illustrating the shaping-based alignment subprocess shown in FIG. 5.

FIG. 7 is a flow chart illustrating the shaping-based alignment subprocess 516 shown in FIG. 5. In this example, the subprocess 516 begins with an initial codeword 412, including EC data 420 and an initial information sequence 414 that may be modified during this subprocess 516. In this example, it is presumed that the codewords 412 of the DNA sequence 402 were encoded using some encoding data or "shaping data" 702, and that shaping data 702 provides some indication as to what sequences of bases can be expected to appear in the information sequences 414.

In one example encoding scheme, the information sequence 414 may be encoded with a simple "paired mapping" of two bases (e.g., A and T) to binary 0 and the other two bases (e.g., G and C) to binary 1, and the encoding process may have alternated between each base in the pair when encoding each binary digit. Such a mapping may be used to, for example, avoid adjacent duplicate bases. For example, a binary string of "111100110110" may be so encoded as "GCGCATGCAGCT", where the adjacent '1' digits alternate between G and C (though both eventually decode to a '1'), and the adjacent '0' digits alternate between A and T (though both eventually decode to a '0'). Such an encoding implies that, in error-free scenarios, adjacent bases should never be the same. Put another way, the presence of two or more of the same base adjacent to each other is an indication of an error (e.g., possibly a substitution error 220 or an indel error 210). For example, the example sequence "GCGCAT" contains no adjacent matching bases, and thus this analysis using encoding data does not indicate the presence of errors (though it should be noted that errors may still be present). In contrast, the sequence "GGCAT" contains two 'G' bases adjacent to each other, a combination which is illegal under this encoding scheme. Such a situation may indicate that a delete error 210B may have occurred with a skew point between the adjacent 'Gs' (or that one of the two 'G' bases is a substitution error). For purposes of discussion, this type of encoding is referred to herein as "alternating bases" encoding.

In another example encoding scheme, the input data used to generate the DNA molecule 402 may have been broken into fixed-length segments (or "tuples") and each of those tuples may be mapped with encoding data that maps each unique tuple to an encoded tuple of a greater length. For example, any occurrence of the tuple "101000" (e.g., as a 6-bit tuple, or the base string "GGA") may be converted into an encoded tuple of "11001000" (e.g., as an 8-bit tuple, or the base string "CAGA"). Such an encoding may, for example, help remove the two adjacent 'G' bases that naturally appeared in the input base string, and thus reducing some potential for error when sequencing and decoding the DNA molecule 402. Such an encoding defines multiple valid encoded tuples of a fixed size (e.g., stored and represented here as the shaping data 702), and thus the appearance of any encoded tuple that is not one of the valid encoded tuples is an indication of some type of error. For purposes of discussion, this type of encoding is referred to herein as a "shaped data" encoding.

At operation 710, the error correction system 130 selects a tuple of the information sequence 414 to inspect. In alternating bases encoding, this tuple may be two or more adjacent bases (e.g., n bases), starting with the first n bases in the information sequence 414, and continuing to shift in an n−1 base sliding window at the next iteration. In shaped data encoding, this tuple is the predetermined size of the encoded tuples (e.g., 4 bases in the above example, or n=4), and continuing to shift in an n base sliding window at the next iteration. For example, presume the beginning of the information sequence 414 is "AAGCGCAT." In an example alternating base encoding, each tuple may be two bases, with the first iteration tuple is the first two bases "AA", the second iteration tuple is the second and third bases "AG", the third tuple is the third and fourth bases "GC", and so forth. In an example shaped data encoding, each tuple may be four bases, with the first iteration tuple being the first four bases "AAGC", the second tuple being the next four bases "GCAT", and so forth.

At operation 712, the error correction system 130 evaluates the current tuple against the shaping data. Under alternating bases encoding, this evaluation operation 712 includes inspecting the tuple for the presence of any adjacent identical bases (e.g., "AA", "TT", "GG", "CC"). The presence of any such adjacent identical base under this encoding is an indication of an error, and an invalid tuple. Under shaped data encoding, this evaluation operation 712 includes comparing the tuple to all of the valid tuples defined by the shaping data 702. If the tuple does not match any of the valid tuples of the shaping data 702, then this is an indication of an error, and an invalid tuple.

At operation 720, if this current tuple is found to be a valid tuple, then the subprocess 516 loops back to operation 710 to select the next tuple and move on through the information sequence 414. If, at operation 720, the current tuple is an invalid tuple, then the error correction system 130 attempts to correct identify whether there is an indel error 210 within or around the area of the tuple (e.g., within the information sequence 414). More specifically, at operation 722 in the example, the error correction system 130 attempts syndrome weight reduction alignment on the tuple by invoking the syndrome weight reduction alignment subprocess 510. The error correction system 130 identifies the range of the tuple within the information sequence 414 (e.g., starting and ending base position) as the suspect region 606 to be inspected and potentially corrected by the syndrome weight reduction alignment subprocess 510. In such an inspection, the subprocess 510 is configured to inspect at least the possible skew points 322 within the area of the tuple, and both insert and delete operations, and may be configured to include skew points within one or more bases before the starting location of the tuple.

Upon conclusion of the subprocess 510, the subprocess 510 returns a response that indicates whether an indel operation was identified that improved the syndrome weight of the information sequence 414. In cases where an indel operation was identified, the subprocess 510 provides information regarding the particular indel operation, as well as a modified information sequence 604 (e.g., a version of the information sequence 414 that includes the indel operation having been performed). At operation 730, if an indel operation is not identified, then the tuple location (e.g., range of the tuple within the information sequence 414) is recorded as a possible unresolved error location, and this data may later be used by other error remediation functions or be passed to the decoding system 125. This subprocess 516 may terminate at this point, or may continue back to operation 710 and iterate again on the next tuple.

Under shaped data encoding, when one tuple remains unresolved at operation 732, this indel may similarly corrupt the analysis of the remaining portion of the information sequence 414 if the fixed n base window continues to be used due to alignment shifting. As such, the next iteration at operation 710 may select the next tuple by finding the next valid tuple to the right of the unresolved tuple (e.g., moving to the right one base at a time and checking that next n base sequence to see if that n-tuple is valid). Once a valid tuple is found, the subprocess 516 may continue forward with that new alignment (e.g., resuming the sliding window at that point).

When an indel operation is identified from the subprocess 510 at operation 730, the error correction system 130 evaluates the altered tuple of the modified information sequence 604 against the shaping data 702. This evaluation may be similar to the evaluation performed at operation 712, but as against the equivalent location within the modified information sequence 604 as the tuple within the original information sequence 414 (e.g., the same or equivalent base positions, depending on whether an insert or delete operation was performed). Operation 740 serves to determine whether the modifications made by the tentative indel operation identified by the subprocess 510 result in this tuple being a valid tuple (e.g., matches one of the encoded tuples within the shaping data, or no longer containing adjacent repeating bases). At operation 742, if the modified tuple is valid, then the modified information sequence 604 is discarded at operation 744 and that tuple location is similarly added as a possible unresolved error location at operation 732.

If, at operation 742, the tuple is valid, then the error correction system 130 retains this indel operation at operation 746 and continues the subprocess 516 with the modified information sequence 604.

The subprocess 516 thus iterates starting at operation 710 with selecting the next tuple. When all tuples of the codeword 412 have been evaluated, then the subprocess 516 exits, returning to the method 500 of FIG. 5.

Figure 8:
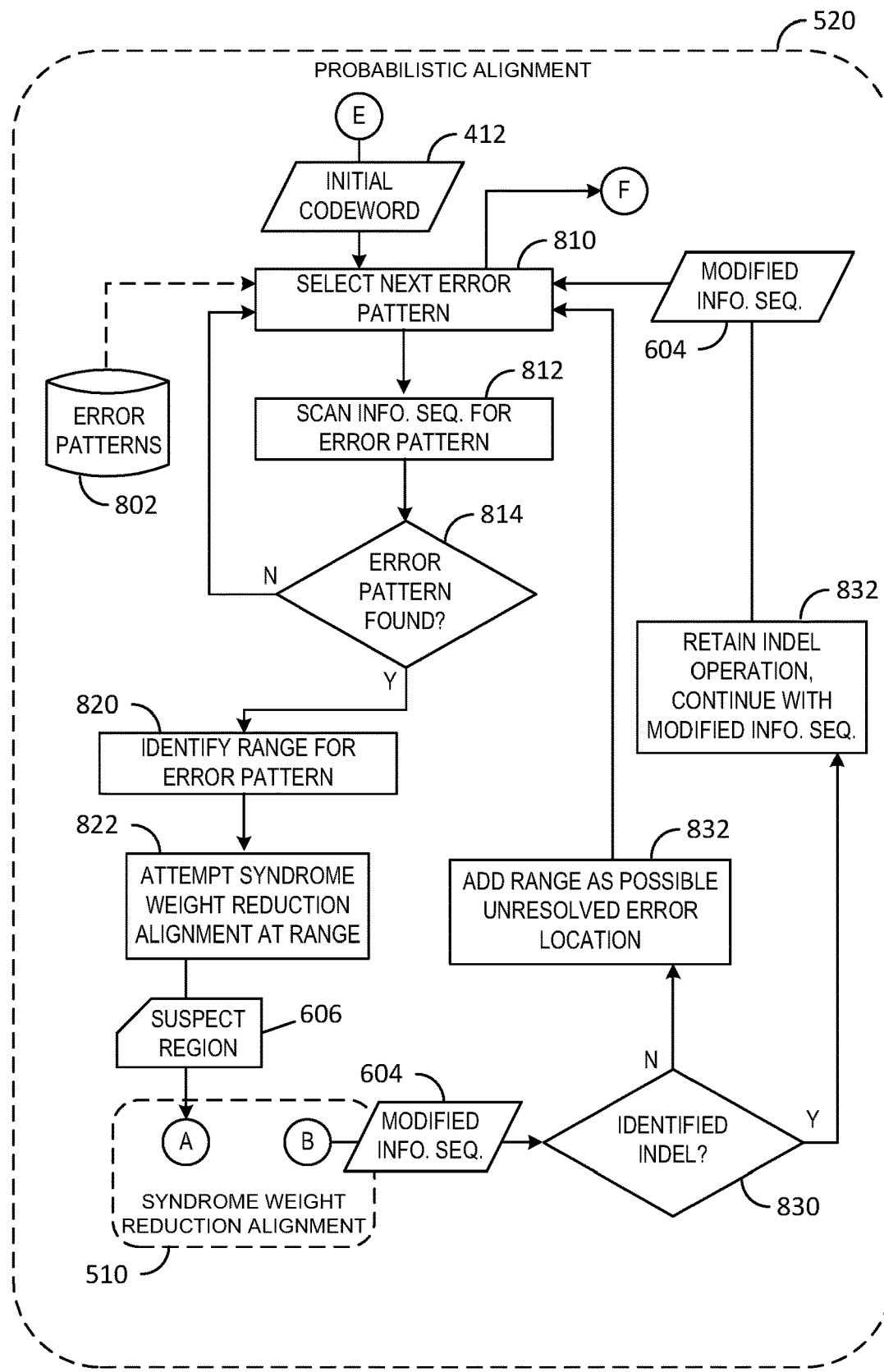
FIG. 8 is a flow chart illustrating the probabilistic alignment subprocess shown in FIG. 5.

FIG. 8 is a flow chart illustrating the probabilistic alignment subprocess 520 shown in FIG. 5. In this example, the subprocess 520 begins with an initial codeword 412, including EC data 420 and an initial information sequence 414 that may be modified during this subprocess 516.

In this example, the subprocess 520 uses a set of predetermined error patterns 802 that may, for example, have been historically collected when identifying past indel or substitution errors during past DNA sequencing and decoding operations. Each of these error patterns 802 include at least a base sequence (e.g., a number of bases, in a particular order, from the base string 304B after a sequencing) that was identified with the error. Each of these error patterns 802 may further include a probability of their occurrence (e.g., as a ratio of the number of times seeing the particular error over a total number of sequencing operations, over a total number of bases, or such), a most common error type and location within that error pattern (e.g., a delete error of a 'T' base between bases 8 and 9), or data regarding particular synthesis and sequencing processes or technologies most typically used during the historical occurrences (e.g., perhaps indicating particular error patterns being associated with particular technologies). Such data may, for example, be collected and evaluated experimentally by synthesizing and sequencing various DNA molecules 402 and comparing the resulting sequenced data 320 with the known original data 310.

At operation 810, the error correction system 130 selects a next error pattern from the error patterns 802. In some examples, this subprocess 520 may be configured to identify a subset of error patterns 802 and this subprocess 520 may iterate on each. In some examples, the subset of error patterns 802 may be selected based on factors such as probability of the error pattern occurring (e.g., with less likely error patterns lending to a higher confidence of error detection when they recur in the codewords 412), or the particular technologies used in the current synthesis or sequencing of the current DNA molecule 402.

At operation 812, the error correction system 130 scans the information sequence 414 for the error pattern. More specifically, in the example, the entirety of the information sequence 414 is scanned for exact occurrences of the current error pattern and the location of any occurrences are identified (e.g., starting base position, ending base position, range of base positions, or the like). At operation 814, if no occurrence of the current error pattern is detected, then the subprocess 520 loops back to operation 810, selects another error pattern and continues processing error patterns until complete.

If, at operation 814, one or more occurrences of the current pattern are detected, then the error correction system 130 identifies a location (e.g., a range of base positions) within the information sequence 414 at which this error pattern occurs. This location data is provided as the suspect region 606 when attempting syndrome weight reduction alignment at operation 822 (e.g., by invoking the syndrome weight reduction alignment subprocess 510).

As discussed above, the syndrome weight reduction alignment subprocess 510 uses the suspect region 606 as the area of focus for indel type errors, searching each possible skew point 322 within the region 606, and postulating both insert and delete type errors at each of those skew points, to determine if an insert or delete error seems to appear (e.g., based on improvement in syndrome weight).

Upon conclusion of the subprocess 510, the subprocess 510 returns a response that indicates whether an indel operation was identified that improved the syndrome weight of the information sequence 414. In cases where an indel operation was identified, the subprocess 510 provides information regarding the particular indel operation (e.g., type, specific location, or the like), as well as a modified information sequence 604 (e.g., a version of the information sequence 414 that includes the indel operation having been performed). At operation 830, if an indel operation is not identified, that suspect region is recorded as a possible unresolved error location at operation 832, and this data may later be used by other error remediation functions or be passed to the decoding system 125. Even though no indel operation was identified in this subprocess 520, the region may still contain an undetected error (though likely a lower error probability than the similar situation in the shaping-based alignment subprocess 516, as the error pattern is a legal pattern to occur in the codeword, where in the shaping-based situation, the pattern is illegal).

If, at operation 830, an indel operation is identified and applied, then the error correction system 130 retains this indel operation at operation 832 and continues the subprocess 520 with the modified information sequence 604.

The subprocess 520 thus iterates starting at operation 810 with selecting the next error pattern. When all error patterns have been evaluated against the information sequence 414, then the subprocess 520 exits, returning to the method 500 of FIG. 5.

FIG. 9 is a flow chart illustrating the length-based alignment subprocess 524 shown in FIG. 5. In this example, the subprocess 520 begins with an initial codeword 412, including EC data 420 and an initial information sequence 414 that may be modified during this subprocess 524. In this example, the subprocess 524 uses a known target length of the information sequence 414 to determine a difference between a number of insert errors and a number delete errors that are present in the information sequence 414. At operation 910, the error correction system 130 identifies a target length for the information sequence 414 from, for example, size data associated with the codeword, the DNA molecule 402, or the like. At operation 912, the error correction system 130 compares a current length of the information sequence 414 to the expected target length.

For example, the expected target length for this information sequence 414 may be 200 bases, but the information sequence 414 of this codeword 412 is currently 198 (e.g., two bases short of the target). This example length data indicates that at least two insert operations are needed to correct for the occurrence of at least two delete errors 210B, as two insert operations would increase the actual length of the information sequence 414 to equal the target length.

Further, it should be noted that one or more insert errors 210A may also have occurred, and thus this length data indicates that, while some delete operations may be needed to counter the insert errors 210A, two more insert operations are needed than delete operations. In other words, while the exact number of needed insert or delete operations is unknown at this point, the difference between the needed insert operations and the needed delete operations is known. If, for example, the length difference is 200 bases (target length)–198 bases (current length)=±2 bases is determined at operation 914, then two more insert operations are needed than the number of delete operations.

At operation 916, the error correction system 130 invokes syndrome weight reduction alignment using this indel difference and/or target length. More specifically, the syndrome weight reduction alignment subprocess 510 is executed with the indel difference or target length as a target for the alignment subprocess 510. This target may, for example, cause the subprocess 510 to try insert operations over delete operations when at a deficit of inserts to deletes, or vice versa. Upon completion of the subprocess 510, the error correction system 130 receives a modified information sequence 604 and verifies that the length of the modified information sequence 604 is equal to the target length at operation 920 before returning to the method 500.

Figure 10:
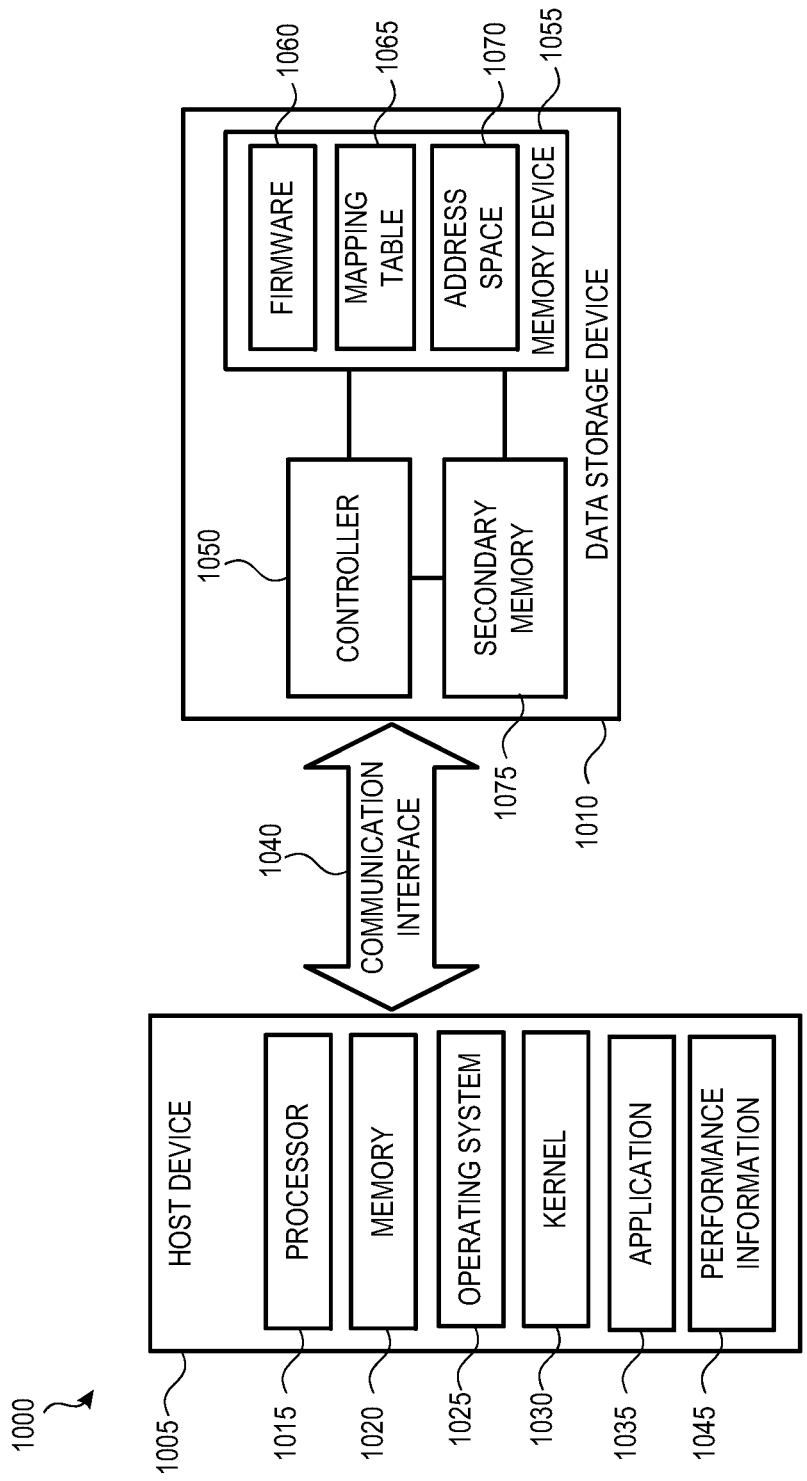
FIG. 10 is a block diagram of a system that includes a host device and a data storage device according to an example.

FIG. 10 is a block diagram of a system 1000 that includes a host device 1005 and a data storage device 1010 according to an example. In an example, the host device 1005 may be similar to the computing device 150 shown and described with respect to FIG. 1, and may be used to perform any or all of the operations described herein. The host device 1005 includes a processor 1015 and a memory device 1020 (e.g., main memory). The memory device 1020 may include an operating system 1025, a kernel 1030 and/or an application 1035.

The processor 1015 can execute various instructions, such as, for example, instructions from the operating system 1025 and/or the application 1035. The processor 1015 may include circuitry such as a microcontroller, a Digital Signal Processor (DSP), an Application-Specific Integrated Circuit (ASIC), a Field Programmable Gate Array (FPGA), hard-wired logic, analog circuitry and/or various combinations thereof. In an example, the processor 1015 may include a System on a Chip (SoC).

In an example, the memory device 1020 can be used by the host device 1005 to store data used by the processor 1015. Data stored in the memory device 1020 may include instructions provided by the data storage device 1010 via a communication interface 1040. The data stored in the memory device 1020 may also include data used to execute instructions from the operating system 1025 and/or one or more applications 1035. In an example, the memory 1020 is volatile memory, such as, for example, Dynamic Random Access Memory (DRAM).

In an example, the operating system 1025 may create a virtual address space for the application 1035 and/or other processes executed by the processor 1015. The virtual address space may map to locations in the memory device 1020. The operating system 1025 may include or otherwise be associated with a kernel 1030. The kernel 1030 may include instructions for managing various resources of the host device 1005 (e.g., memory allocation), handling read and write requests and so on.

The communication interface 1040 communicatively couples the host device 1005 and the data storage device 1010. The communication interface 1040 may be a Serial Advanced Technology Attachment (SATA), a PCI express (PCIe) bus, a Small Computer System Interface (SCSI), a Serial Attached SCSI (SAS), Ethernet, Fibre Channel, or WiFi. As such, the host device 1005 and the data storage device 1010 need not be physically co-located and may communicate over a network such as a Local Area Network (LAN) or a Wide Area Network (WAN), such as the internet. In addition, the host device 1005 may interface with the data storage device 1010 using a logical interface specification such as Non-Volatile Memory express (NVMe) or Advanced Host Controller Interface (AHCI).

The data storage device 1010 includes a controller 1050 and a memory device 1055 (e.g. volatile and/or non-volatile memory). The memory device 1055 (and/or portions of the memory device 1055) may also be referred to as a storage medium. The memory device 1055 includes a number of storage elements. In an example, each storage element is a chip or a memory die that is used to store data.

For example, the memory device 1055 may include a first memory die and a second memory die. In an example, the first memory die and the second memory die include non-volatile memory elements such as, for example, NAND flash memory elements and/or NOR flash memory elements. Although two memory dies are mentioned, the memory device 1055 may include any number of storage elements. For example, the storage elements may take the form of solid-state memory such as, for example, 2D NAND, 3D NAND memory, multi-level cell memory, triple level cell memory, quad-level cell memory, penta-level cell memory or any combination thereof.

The controller 1050 may include circuitry for executing instructions. The instructions may originate from firmware 1060 associated with the data storage device 1010. In another example, the instructions may originate from the host device 1005. Accordingly, the controller 1050 may include circuitry such as one or more processors, a microcontroller, a DSP, an ASIC, an FPGA, hard-wired logic, analog circuitry and/or a combination thereof. In another example, the controller 1050 may include a SoC.

The data storage device 1010 may also include secondary memory 1075. The secondary memory 1075 may be a rotating magnetic disk or non-volatile solid-state memory, such as flash memory. While the description herein refers to solid-state memory generally, it is understood that solid-state memory may comprise one or more of various types of memory devices such as flash integrated circuits, NAND memory (e.g., single-level cell (SLC) memory, multi-level cell (MLC) memory (i.e., two or more levels), or any combination thereof), NOR memory, EEPROM, other discrete Non-Volatile Memory (NVM) chips, or any combination thereof.

In some examples, the memory device 1055 is capable of storing data at a byte-addressable level, as opposed to other types of non-volatile memory that have a smallest writable data size such as a page size of 4 KB or a sector size of 512 Bytes.

In some examples, the memory device 1055 may also store a mapping table 1065 and/or an address space 1070. In some examples, the controller 1050 can associate portions of data stored in the secondary memory 1075 with unique identifiers. The unique identifiers may be stored in the memory device 1055 and be used by the operating system 1025 to access stored data. For example, the mapping table 1065 can provide a mapping of unique identifiers with indications of physical locations (e.g., Physical Block Addresses (PBAs)) where the corresponding portions of data are stored in the memory device 1055 and/or the secondary memory 1075.

In some examples, the firmware 1060 may store, maintain, be associated with or otherwise have access to a mapping table (e.g., mapping table 1065) that stores and/or maintains mapping information for the various DNA sequences such as described above.

As briefly discussed above, the memory device 1055 may also include address space 1070. The address space 1070 can serve as at least a portion of an address space used by the processor 1015. In an example, the address space 1070 can store data at a byte-addressable level that can be accessed by the processor 1015 (e.g., via the communication interface 1040).

For example, the data storage device 1010 may provide the host device 1005 with an indication of the address space 1070. The host device 1005 may then associate an address range for the address space 1070 and an indication that this address range is to be used as a byte-addressable address space, such as for a page cache.

In another example, the host device 1005 may manage the data storage device 1010 such that the processor 1015 can directly access address space 1070. For example, the data storage device 1010 may provide logical to physical address translation information to the host device 1005, which can be called by the host device 1005 and executed by the processor 1015 and/or the controller 1050. In some examples, the controller 1050 may include or otherwise be associated with a flash translation layer (FTL). The FTL may map the logical block addresses to the physical addresses of the memory device 1055.

Although FIG. 10 illustrates the host device 1005 being separate from the data storage device 1010, the host device 1005 and the data storage device 1010, as well the various components described, may be part of a single device or part of multiple devices.

Based on the above, examples, of the present application describe a DNA-based storage system, comprising: an error correction system operable to: identify a DNA codeword from an output string produced from a DNA sequencing operation on a DNA molecule, the DNA codeword including at least an information segment and an associated error correction segment; calculate an initial syndrome weight for the information segment based on error correction data included in the error correction segment; determine whether the initial syndrome weight is greater than a predetermined threshold; based on determining the initial syndrome weight is greater than the predetermined threshold, perform an alignment alteration in the information segment by: selecting a skew point within the information segment; performing an indel operation on the information segment at the skew point, thereby generating a modified information segment; calculating a modified syndrome weight of the modified information segment based on the error correction data; comparing the initial syndrome weight with the modified syndrome weight; and incorporating the indel operation into the information segment when the comparing indicates an improvement in the modified syndrome weight, thereby generating a modified codeword; decode the modified codeword to generate at least a portion of an output file, the portion including data decoded from the modified information segment; and transmit contents of the output file to a computing device, the output file representing user data stored within the DNA molecule. In an example, the indel operation is an insert operation and wherein performing the indel operation further comprises: shifting, to the right by one base position, all of the DNA bases occurring after the skew point within the information segment; and inserting a new DNA base at the skew point. In an example, the indel operation is a delete operation and wherein performing the indel operation further comprises: deleting, from the information segment, an existing DNA base adjacent to the skew point; and shifting, to the left by one base position, all of the DNA bases occurring after the skew point within the information segment. In an example, the error correction system is further operable to: determine whether there is known shaping data associated with the DNA codeword; and based on determining there is known shaping data associated with the DNA codeword: select a first tuple of DNA bases from the information segment, the first tuple occupying a first region of the information segment; compare the first tuple of DNA bases to a set of valid tuples, thereby identifying that the first tuple is invalid; and perform one or more indel operations at one or more skew points within the first region. In an example, the indel operation is a first indel operation and the error correction system is further operable to incorporate a second indel operation of the one or more indel operations into the information segment based on determining the second indel operation results in an improved syndrome weight for the information segment. In an example, the error correction system is further operable to: scan the information segment for an occurrence of one or more error patterns, each error pattern including an ordered sequence of DNA bases; identify, within the information segment, a first occurrence of a first error pattern based on the scanning, the first occurrence occupying a first region of the information segment; and perform one or more indel operations at one or more skew points within the first region. In an example, the error correction system is further operable to: identify an expected length of the information segment; determine a current length of the information segment from the codeword; compute a difference between the expected length and the current length; and perform a number of insert operations and a number of delete operations based on the difference, where the performance results in a modified information segment that has a length equal to the expected length.

Examples of the present application also describe a method for performing error correction on a DNA codeword generated through sequencing a DNA molecule, the method comprising: identifying a DNA codeword from an output string produced from a DNA sequencing operation on a DNA molecule, the DNA codeword including at least an information segment and an associated error correction segment; calculating an initial syndrome weight for the information segment based on error correction data included in the error correction segment; determining whether the initial syndrome weight is greater than a predetermined threshold; and based on determining the initial syndrome weight is greater than the predetermined threshold, performing an alignment alteration in the information segment by: selecting a skew point within the information segment; performing an indel operation on the information segment at the skew point, thereby generating a modified information segment; calculating a modified syndrome weight of the modified information segment based on the error correction data; comparing the initial syndrome weight with the modified syndrome weight; and incorporating the indel operation into the information segment when the comparing indicates an improvement in the modified syndrome weight, thereby generating a modified codeword. In an example, the indel operation is an insert operation, wherein performing the indel operation further comprises: shifting, to the right by one base position, all of the DNA bases occurring after the skew point within the information segment; and inserting a new DNA base at the skew point. In an example, the indel operation is a delete operation, wherein performing the indel operation further comprises: deleting, from the information segment, an existing DNA base adjacent to the skew point; and shifting, to the left by one base position, all of the DNA bases occurring after the skew point within the information segment. In an example, the method further comprises determining whether there is known shaping data associated with the DNA codeword; and based on determining there is known shaping data associated with the DNA codeword: selecting a first tuple of DNA bases from the information segment, the first tuple occupying a first region of the information segment; comparing the first tuple of DNA bases to a set of valid tuples, thereby identifying that the first tuple is invalid; and performing one or more indel operations at one or more skew points within the first region. In an example, the indel operation is a first indel operation and the method further comprises incorporating a second indel operation of the one or more indel operations into the information segment when the second indel operation results in an improved syndrome weight for the information segment. In an example, the method further comprises scanning the information segment for an occurrence of one or more error patterns, each error pattern including an ordered sequence of DNA bases; identifying, within the information segment, a first occurrence of a first error pattern based on the scanning, the first occurrence occupying a first region of the information segment; and performing one or more indel operations at one or more skew points within the first region. In an example, the method further comprises identifying an expected length of the information segment; determining a current length of the information segment from the codeword; computing a difference between the expected length and the current length; and performing a number of insert operations and a number of delete operations based on the difference, where the performance results in a modified information segment that has a length equal to the expected length.

Examples of the present application also describe a control system for a DNA-based storage system, comprising: means for identifying a DNA codeword from an output string produced from a DNA sequencing operation on a DNA molecule, the DNA codeword including at least an information segment and an associated error correction segment; means for calculating an initial syndrome weight for the information segment based on error correction data included in the error correction segment; means for determining that the initial syndrome weight is greater than a predetermined threshold; and in response to the determining, means for performing an alignment alteration in the information segment. In an example, the alignment alteration includes performance of a indel operation, the indel operation being an insert operation, wherein performing the indel operation further includes: shifting, to the right by one base position, all of the DNA bases occurring after a skew point within the information segment; and inserting a new DNA base at the skew point. In an example, the alignment alteration includes performance of a indel operation, the indel operation being a delete operation, wherein performing the indel operation further includes: deleting, from the information segment, an existing DNA base adjacent to a skew point; and shifting, to the left by one base position, all of the DNA bases occurring after the skew point within the information segment. In an example, the control system further comprises means for determining whether there is known shaping data associated with the DNA codeword; means for selecting a first tuple of DNA bases from the information segment, the first tuple occupying a first region of the information segment; means for comparing the first tuple of DNA bases to a set of valid tuples, thereby identifying that the first tuple is invalid; and means for performing one or more indel operations at one or more skew points within the first region. In an example, the indel operation is a first indel operation wherein the control system further comprises means for incorporating a second indel operation of the one or more indel operations into the information segment when the second indel operation results in an improved syndrome weight for the information segment. In an example, the control system further comprises: means for scanning the information segment for an occurrence of one or more error patterns, each error pattern includes an ordered sequence of DNA bases; means for identifying, within the information segment, a first occurrence of a first error pattern based on the scanning, the first occurrence occupying a first region of the information segment; and means for performing one or more indel operations at one or more skew points within the first region.

The term computer-readable media as used herein may include computer storage media. Computer storage media may include volatile and nonvolatile, removable and non-removable media implemented in any method or technology for storage of information, such as computer readable instructions, data structures, or program modules. Computer storage media may include RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other article of manufacture which can be used to store information and which can be accessed by a computing device. Any such computer storage media may be part of the computing device. Computer storage media does not include a carrier wave or other propagated or modulated data signal.

Additionally, examples described herein may be discussed in the general context of computer-executable instructions residing on some form of computer-readable storage medium, such as program modules, executed by one or more computers or other devices. By way of example, and not limitation, computer-readable storage media may comprise non-transitory computer storage media and communication media. Generally, program modules include routines, programs, objects, components, data structures, etc., that perform particular tasks or implement particular abstract data types. The functionality of the program modules may be combined or distributed as desired in various examples.

Communication media may be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media.

The description and illustration of one or more aspects provided in the present disclosure are not intended to limit or restrict the scope of the disclosure in any way. The aspects, examples, and details provided in this disclosure are considered sufficient to convey possession and enable others to make and use the best mode of claimed disclosure.

The claimed disclosure should not be construed as being limited to any aspect, example, or detail provided in this disclosure. Regardless of whether shown and described in combination or separately, the various features (both structural and methodological) are intended to be selectively rearranged, included or omitted to produce an example with a particular set of features. Having been provided with the description and illustration of the present application, one skilled in the art may envision variations, modifications, and alternate aspects falling within the spirit of the broader aspects of the general inventive concept embodied in this application that do not depart from the broader scope of the claimed disclosure.

Aspects of the present disclosure have been described above with reference to schematic flowchart diagrams and/or schematic block diagrams of methods, apparatuses, systems, and computer program products according to examples of the disclosure. It will be understood that each block of the schematic flowchart diagrams and/or schematic block diagrams, and combinations of blocks in the schematic flowchart diagrams and/or schematic block diagrams, can be implemented by computer program instructions. These computer program instructions may be provided to a processor of a computer or other programmable data processing apparatus to produce a machine, such that the instructions, which execute by way of the processor or other programmable data processing apparatus, create means for implementing the functions and/or acts specified in the schematic flowchart diagrams and/or schematic block diagrams block or blocks.

References to an element herein using a designation such as "first," "second," and so forth does not generally limit the quantity or order of those elements. Rather, these designations may be used as a method of distinguishing between two or more elements or instances of an element. Thus, reference to first and second elements does not mean that only two elements may be used or that the first element precedes the second element. Additionally, unless otherwise stated, a set of elements may include one or more elements.

Terminology in the form of "at least one of A, B, or C" or "A, B, C, or any combination thereof" used in the description or the claims means "A or B or C or any combination of these elements." For example, this terminology may include A, or B, or C, or A and B, or A and C, or A and B and C, or 2A, or 2B, or 2C, or 2A and B, and so on. As an additional example, "at least one of: A, B, or C" is intended to cover A, B, C, A-B, A-C, B-C, and A-B-C, as well as multiples of the same members. Likewise, "at least one of: A, B, and C" is intended to cover A, B, C, A-B, A-C, B-C, and A-B-C, as well as multiples of the same members.

Similarly, as used herein, a phrase referring to a list of items linked with "and/or" refers to any combination of the items. As an example, "A and/or B" is intended to cover A alone, B alone, or A and B together. As another example, "A, B and/or C" is intended to cover A alone, B alone, C alone, A and B together, A and C together, B and C together, or A, B, and C together.

What is claimed is:

1. A deoxyribonucleic acid (DNA)-based storage system, comprising:
   an error correction system operable to:
   identify a DNA codeword, the DNA codeword including an information segment and an error correction segment;
   calculate an initial syndrome weight for the information segment based, at least in part, on error correction data included in the error correction segment;

determine whether the initial syndrome weight is greater than a predetermined threshold; and perform an alignment alteration in the information segment based, at least in part, on determining that the initial syndrome weight is greater than the predetermined threshold, wherein performing the alignment alteration corrects one or more insertion/deletion (indel) errors in the information segment.

2. The DNA-based storage system of claim 1, wherein performing the alignment alteration comprises:

selecting a skew point within the information segment;

performing an indel operation on the information segment at the skew point to generate a modified information segment;

calculating a modified syndrome weight of the modified information segment based, at least in part, on the error correction data;

comparing the initial syndrome weight with the modified syndrome weight; and generating a modified codeword by incorporating the indel operation into the information segment based, at least in part, on the comparison between the initial syndrome weight and the modified syndrome weight.

3. The DNA-based storage system of claim 1, wherein the indel operation is a deletion operation and wherein performing the indel operation further comprises:

deleting, from the information segment, an existing DNA base adjacent to the skew point; and shifting all DNA bases occurring after the skew point within the information segment by at least one base position.

4. The DNA-based storage system of claim 1, wherein the error correction system is further operable to:

determine whether there is known shaping data associated with the DNA codeword; and based, at least in part, on determining that there is known shaping data associated with the DNA codeword:

select a first tuple of DNA bases from the information segment, the first tuple of DNA bases occupying a first region of the information segment;

compare the first tuple of DNA bases to a set of valid tuples, thereby identifying that the first tuple is invalid; and perform one or more indel operations at one or more skew points within the first region.

5. The DNA-based storage system of claim 4, wherein the performed one or more indel operations is a first indel operation and wherein the error correction system is further operable to incorporate a second indel operation of the one or more indel operations into the information segment based, at least in part, on determining that the second indel operation results in an improved syndrome weight for the information segment.

6. The DNA-based storage system of claim 1, wherein the error correction system is further operable to:

scan the information segment for an occurrence of one or more error patterns, each error pattern including an ordered sequence of DNA bases;

identify, within the information segment, a first occurrence of a first error pattern based, at least in part, on the scanning, the first occurrence occupying a first region of the information segment; and perform one or more indel operations at one or more skew points within the first region.

7. The DNA-based storage system of claim 1, wherein the error correction system is further operable to:

identify an expected length of the information segment;

determine a current length of the information segment from the codeword;

compute a difference between the expected length and the current length; and perform a number of insertion operations and a number of deletion operations based, at least in part, on the difference, where the performance of the number of insertion operations and the number of deletion operations results in a modified information segment that has a length equal to the expected length.

8. The DNA-based storage system of claim 1, wherein the indel operation is an insertion operation and wherein performing the indel operation further comprises:

shifting all DNA bases occurring after the skew point within the information segment by the at least one base position; and inserting a new DNA base at the skew point.

9. The DNA-based storage system of claim 2, wherein the error correction system is further operable to:

decode the modified codeword to generate at least a portion of an output file, the portion of the output file including data decoded from the modified information segment; and transmit contents of the output file to a computing device, the output file representing user data associated with the DNA codeword.

10. A method for performing error correction on a deoxyribonucleic acid (DNA) codeword generated through sequencing a DNA molecule, the method comprising:

identifying a DNA codeword, the DNA codeword including at least an information segment and an associated error correction segment;

calculating an initial syndrome weight for the information segment based, at least in part, on error correction data associated with the error correction segment;

determining whether the initial syndrome weight is greater than a predetermined threshold; and performing an alignment alteration in the information segment based, at least in part, on determining that the initial syndrome weight is greater than the predetermined threshold, wherein performing the alignment alteration corrects one or more insertion/deletion (indel) errors in the information segment.

11. The method of claim 8, further comprising:

determining whether there is known shaping data associated with the DNA codeword; and based, at least in part, on determining that there is known shaping data associated with the DNA codeword:

selecting a first tuple of DNA bases from the information segment, the first tuple of DNA bases occupying a first region of the information segment;

comparing the first tuple of DNA bases to a set of valid tuples, thereby identifying that the first tuple is invalid; and performing one or more indel operations at one or more skew points within the first region.

12. The method of claim 11, wherein the performed one or more indel operation is a first indel operation and wherein the method further comprises incorporating a second indel operation of the one or more indel operations into the information segment responsive to the second indel operation resulting in an improved syndrome weight for the information segment.

13. The method of claim 8, further comprising:
scanning the information segment for an occurrence of one or more error patterns, each error pattern including an ordered sequence of DNA bases;
identifying, within the information segment, a first occurrence of a first error pattern based, at least in part, on the scanning, the first occurrence occupying a first region of the information segment; and
performing one or more indel operations at one or more skew points within the first region.

14. The method of claim 8, further comprising:
identifying an expected length of the information segment;
determining a current length of the information segment from the codeword;
computing a difference between the expected length and the current length; and
performing a number of insertion operations and a number of deletion operations based, at least in part, on the difference, where the performance results in a modified information segment that has a length equal to the expected length.

15. The method of claim 10, wherein performing the alignment alteration comprises:
selecting a skew point within the information segment;
performing an indel operation on the information segment at the skew point to generate a modified information segment;
calculating a modified syndrome weight of the modified information segment based, at least in part, on the error correction data;
comparing the initial syndrome weight with the modified syndrome weight; and
generating a modified codeword by incorporating the indel operation into the information segment based, at least in part, on the comparison between the initial syndrome weight and the modified syndrome weight.

16. The method of claim 15, wherein the indel operation is an insertion operation and wherein performing the indel operation further comprises:
shifting all DNA bases occurring after the skew point within the information segment by at least one base position; and
inserting a new DNA base at the skew point.

17. The method of claim 15, wherein the indel operation is a deletion operation and wherein performing the indel operation further comprises:
deleting, from the information segment, an existing DNA base adjacent to the skew point; and
shifting all of the DNA bases occurring after the skew point within the information segment by at least one base position.

18. The method of claim 15, wherein the indel operation is incorporated into the information segment based, at least in part, on the comparing the initial syndrome weight with the modified syndrome weight indicating an improvement in the modified syndrome weight when compared to the initial syndrome weight.

19. A control system for a deoxyribonucleic acid (DNA)-based storage system, the control system
means for identifying a DNA codeword from an output string produced from a DNA sequencing operation on a DNA molecule, the DNA codeword including an information segment and an associated error correction segment;
means for calculating an initial syndrome weight for the information segment based, at least in part, on error correction data included in the error correction segment;
means for determining whether the initial syndrome weight is greater than a predetermined threshold; and
means for performing, based at least in part on the determining, an alignment alteration in the information segment.

20. The control system of claim 15, wherein the control system further comprises:
means for scanning the information segment for an occurrence of one or more error patterns, each error pattern including an ordered sequence of DNA bases;
means for identifying, within the information segment, a first occurrence of a first error pattern based, at least in part, on the scanning, the first occurrence occupying a first region of the information segment; and
means for performing one or more insertion/deletion (indel) operations at one or more skew points within the first region.

* * * * *